(12) United States Patent
Zaid et al.

(10) Patent No.: US 12,419,872 B2
(45) Date of Patent: *Sep. 23, 2025

(54) LOW-TEMPERATURE SYNTHESIS OF THYMOQUINONE AND HARMALINE COMPOUNDS

(71) Applicant: Ankh Life Sciences Limited, Dublin (IE)

(72) Inventors: Gene H. Zaid, Hutchinson, KS (US); Beth Ann Wolf, Hutchinson, KS (US); Rachel Elizabeth Ropp, Hutchinson, KS (US); Krishna Mohan Donavalli, Sterling, KS (US); Rajni Verma, Sterling, KS (US)

(73) Assignee: Ankh Life Sciences Limited, Dublin (IE)

( * ) Notice: Subject to any disclaimer, the term of this patent is extended or adjusted under 35 U.S.C. 154(b) by 727 days.

This patent is subject to a terminal disclaimer.

(21) Appl. No.: 17/670,264

(22) Filed: Feb. 11, 2022

(65) Prior Publication Data

US 2022/0160685 A1    May 26, 2022

Related U.S. Application Data

(63) Continuation-in-part of application No. 16/810,291, filed on Mar. 5, 2020, now Pat. No. 11,358,963.

(51) Int. Cl.
   *A61K 31/437*      (2006.01)
(52) U.S. Cl.
   CPC .................. *A61K 31/437* (2013.01)
(58) Field of Classification Search
   CPC .................................................. A61K 31/437
   See application file for complete search history.

(56) References Cited

U.S. PATENT DOCUMENTS

| | | | |
|---|---|---|---|
| 2,616,893 A | 11/1952 | Newby | |
| 5,304,658 A | 4/1994 | Terao et al. | |
| 9,630,899 B1 | 4/2017 | Huang et al. | |
| 10,875,859 B2 * | 12/2020 | Zaid | A61P 35/00 |
| 11,358,963 B2 * | 6/2022 | Zaid | C07D 471/04 |
| 11,452,715 B2 * | 9/2022 | Zaid | A61K 31/437 |
| 11,453,664 B2 * | 9/2022 | Zaid | C07D 471/04 |
| 11,453,665 B2 * | 9/2022 | Zaid | C07D 471/04 |
| 2015/0037308 A1 | 2/2015 | Ikemoto et al. | |
| 2019/0315742 A1 | 10/2019 | Zaid et al. | |
| 2020/0101050 A1 | 4/2020 | Zaid et al. | |
| 2020/0102305 A1 | 4/2020 | Zaid et al. | |
| 2020/0102306 A1 | 4/2020 | Zaid et al. | |

FOREIGN PATENT DOCUMENTS

| | | |
|---|---|---|
| WO | 2016064676 A1 | 4/2016 |
| WO | 2019200107 A1 | 10/2019 |

OTHER PUBLICATIONS

International Search Report and Written Opinion in PCT/US2021/020847, filed Mar. 4, 2021.
Office Action dated Apr. 1, 2020 in U.S. Appl. No. 16/380,279, now U.S. Pat. No. 10,875,859 issued Dec. 29, 2020.
Office Action dated Aug. 27, 2020 in U.S. Appl. No. 16/380,279, now U.S. Pat. No. 10,875,859 issued Dec. 29, 2020.
Office Action dated Dec. 17, 2021 in U.S. Appl. No. 16/701,554, now U.S. Pat. No. 11,453,664 issued Sep. 27, 2022.
Office Action dated Dec. 17, 2021 in U.S. Appl. No. 16/701,581, now U.S. Pat. No. 11,453,665 issued Sep. 27, 2022.
Office Action dated Dec. 16, 2021 in U.S. Appl. No. 16/701,597, now U.S. Pat. No. 11,452,715 issued Sep. 27, 2022.

* cited by examiner

*Primary Examiner* — D Margaret M Seaman
(74) *Attorney, Agent, or Firm* — Hovey Williams LLP; Crissa A. Cook

(57) ABSTRACT

Low-temperature syntheses of thymoquinone/harmaline compounds which are useful for the treatment of human diabetes and cancers, and the derivatives, solvates, prodrugs, isomers, and tautomers of such compounds.

11 Claims, 12 Drawing Sheets

LOW-TEMPERATURE SYNTHESIS OF THYMOQUINONE AND HARMALINE COMPOUNDS

CROSS-REFERENCE TO RELATED APPLICATIONS

This application is a continuation-in-part of U.S. patent application Ser. No. 16/810,291, filed Mar. 5, 2020, which is incorporated by reference herein in its entirety.

BACKGROUND OF THE INVENTION

Field of the Invention

The present invention is concerned with new synthesis methods for the preparation of thymoquinone/harmaline adducts or compounds. More particularly, the invention is concerned with low-temperature synthesis techniques which provide greater quantities of desirable thymoquinone/harmaline compounds having molecular weights of about 360 to 380.

SUMMARY OF THE INVENTION

U.S. Patent Publication 2019/0315742 and U.S. patent application Ser. No. 16/701,554 filed Dec. 3, 2019 (both of which are incorporated by reference herein in their entireties), describe adducts or compounds of thymoquinone (TQ) and harmaline and related harmaline-like compounds. These reaction products show significant promise as treatments for human diabetes and cancers. These references teach that the adducts or compounds are prepared by mixing together TQ and harmaline (or harmaline-like material(s)) in an organic solvent, such as a C1-C4 lower alcohol (e.g., ethanol) and/or dimethyl sulfoxide (DMSO), followed by allowing the reaction mixture to stand for a period of from about 12 hours-4 weeks at a temperature ranging from about 20-60° C. The most preferred reaction conditions involve standing for 24 hours at room temperature. However, these reactions yield very low quantities of the desirable reaction products having molecular weights of 360, 376, and 378, normally less than 20% by weight. Furthermore, these higher temperature reactions lead to significant quantities of higher molecular weight species above MW 500, which must be separated from the desired end products.

The present invention overcomes these difficulties, and provides improved methods for synthesis of TQ/harmaline reaction products, in good yields. Generally speaking, the methods of the invention comprise the steps of mixing together thymoquinone and harmaline in a noninterfering solvent, and carrying out the reaction between thymoquinone and harmaline at a temperature of less than about 10° C. Desirably, the reaction temperature is less than about 0° C., and more preferably ranges from about −10° C. to about −100° C. The reaction time is usually for a period of from about 4 hours to about 14 days, and more preferably from about 6-100 hours. Advantageously, the low-temperature conditions are maintained throughout the reaction period.

The methods hereof preferably involve carrying out the TQ/harmaline reaction so that the amount of reaction products having a molecular weight ranging from about 360-380, and in particularly reaction products having respective molecular weights of about 360 and about 378, is greater than the amount of any other reaction product of different molecular weights. Furthermore, at least about 35% by weight of the reaction products have molecular weights ranging from about 360-380, and in particularly at least about 35% by weight of the reaction products have molecular weights of about 360 and/or about 378. Still more preferably, the reactions are carried out so that the total amount of the reaction products having molecular weights of about 376 and about 378 (preferably about 378) is at least about 25% by weight of the reaction products, and more preferably at least about 30% by weight thereof. A variety of noninterfering solvents may be used in the invention, although those selected from the group consisting of a C1-C4 alcohol, dimethyl sulfoxide, and mixtures thereof, are preferred.

The desirable molecular weight reaction products may include tautomers and isomers, as explained below. Furthermore, the reaction products may be readily modified or derivatized to provide solvates, esters, metal complexes (e.g., Cu, Fe, Zn, Pt, V), and salts of the reaction products.

DETAILED DESCRIPTION OF THE PREFERRED EMBODIMENTS

Figure 1:
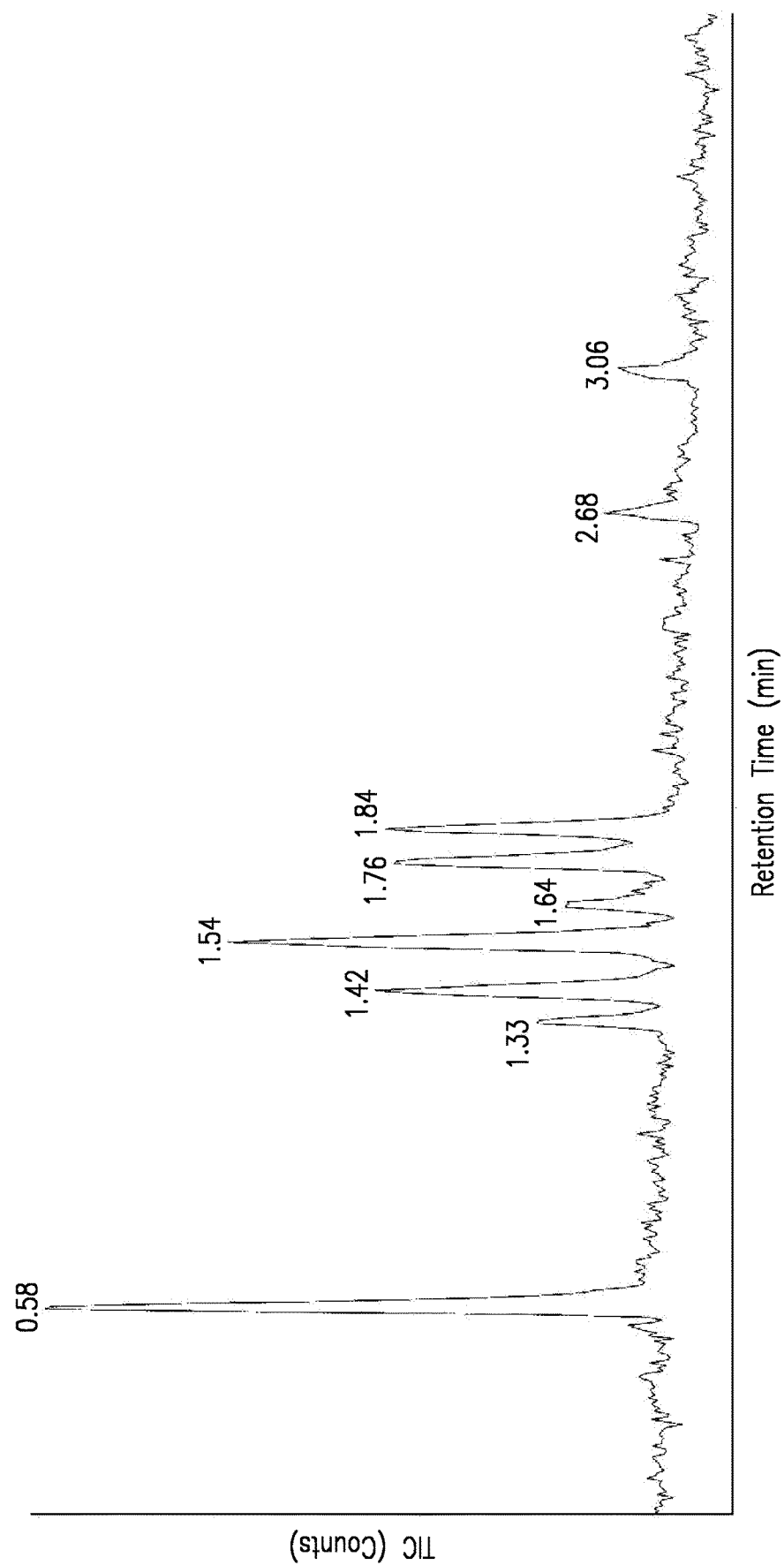
FIG. 1 is a spectrum derived from the assay described in Example 1.

Thymoquinone, $C_{10}H_{12}O_2$, is identified as CAS #490-91-5, and has a molecular weight of 164.2. It has the structure

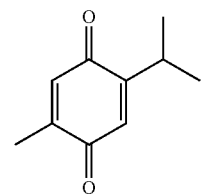

Harmaline (7-methoxy-1-1-methyl-4,9-dihydro-3H-pyrido[3,4-b]indole) is a fluorescent psychoactive alkaloid from the group of harmala alkaloids and β-carbolines, and occurs in various plants, such as *Peganum harmala*. Harmaline is identified as CAS #304-21-2, and exists in two tautomeric forms:

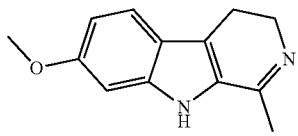

7-methoxy-1-methyl-4,9-dihydro-3H-pyrido[3,4-b]indole
Chemical Formula: $C_{13}H_{14}N_2O$
Exact Mass: 214.11

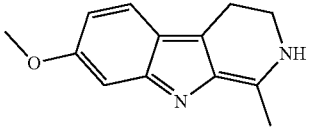

7-methoxy-1-methyl-3,4-dihydro-2H-pyrido[3,4-b]indole
Chemical Formula: $C_{13}H_{14}N_2O$
Exact Mass: 214.11

Moreover, in solution, harmaline is prone to further tautomerism, resulting in constitutional isomers, which can interconvert in a rapid equilibrium where the location of a given double bond rotates or flips:

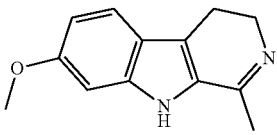

Chemical Formula: $C_{13}H_{14}N_2O$
Exact Mass: 214.11
Imine Form

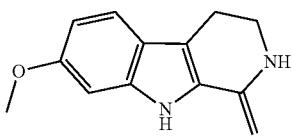

Chemical Formula: $C_{13}H_{14}N_2O$
Exact Mass: 214.11
Enamine Form

As used herein, "harmaline" refers to any such isomers or tautomers.

In preparing the reaction product compositions of the invention, use should be made of ingredients of relatively high purity, typically at least about 90% by weight pure, and more preferably at least about 98% by weight pure. The use of naturally occurring sources for the ingredients is generally not appropriate or desirable, because these naturally occurring products contain relatively small amounts of the desired components and/or have potentially interfering compounds therein. Use of low-purity ingredients often leads to little or no reaction products in accordance with the invention.

Thus, the preferred TQ and harmaline starting compounds or components of the invention are either synthetically derived or derived from one or more naturally occurring product(s) which have been significantly modified so as to contain at least about 90% by weight (more preferably at least about 98% by weight) of the desired component. As used herein, "synthetically derived" means that the component in question was synthesized using specific starting ingredients and one or more chemical and/or biological reactions to obtain substantially pure compounds. Modification of naturally occurring products may involve extractions, or any other physical or chemical steps to achieve the desired end product.

The improved methods for synthesis of TQ/harmaline reaction products having increased yields, comprise the steps of mixing together thymoquinone and harmaline in a noninterfering solvent, preferably an organic solvent, such as a C1-C4 lower alcohol (e.g., ethanol), dimethyl sulfoxide (DMSO), or a mixture thereof. Preferably, the thymoquinone and harmaline are mixed together in a weight ratio of from about 1:0.1 to about 1:5 (preferably from about 1:0.1 to about 1:2), followed by stirring until each component is dissolved in solution. The thymoquinone and harmaline are allowed to react in solution at a temperature of less than about 10° C. Preferably, the reaction solution is allowed to rest under these low-temperature conditions for the desired reaction time, and continuous mixing is not required. Desirably, the reaction temperature is less than about 0° C., more preferably from about -10° C. to about -100° C., more preferably from about -18° C. to about -100° C., and even more preferably from about -40° C. to about -80° C. The reaction time is usually for a period of from about 4 hours to about 14 days, and more preferably from about 6 hours to about 100 hours, even more preferably from about 8 hours to about 72 hours. Advantageously, the low-temperature conditions are maintained throughout the reaction period. The reaction can be carried out in the presence or absence of light. After the reaction products are obtained, the reactant solution can be allowed to return to room temperature (~20-25° C.). The reaction products can be extracted from the reaction solution. In one or more embodiments, the reaction products (solids) can be extracted or precipitated from the reaction solution using aqueous and/or organic solvents, including deionized (DI) water and/or sodium bicarbonate. In one or more embodiments, the reaction products can be extracted via recrystallization using solvent, such as ethanol or methanol.

The methods hereof preferably involve carrying out the TQ/harmaline reaction so that the amount of reaction products having a molecular weight ranging from about 360-380, and in particularly reaction products having respective molecular weights of about 360 and about 378, is greater than the amount of any other reaction product of different molecular weights. Furthermore, at least about 35% by weight of the reaction products (preferably at least 40%, preferably at least 50% by weight) have molecular weights ranging from about 360-380, and in particularly at least about 35% by weight (preferably at least 40%, preferably at least 50% by weight) of the reaction products in the resulting reactant solution have molecular weights of about 360 and/or about 378. Still more preferably, the reactions are carried out so that the total amount of the reaction products having molecular weights of between about 376 and about 378 (preferably about 378) is at least about 25% by weight of the reaction products, and more preferably at least about 30% by weight thereof.

TQ/Harmaline Reaction Products

An analysis of the reaction products reveals that some products described below have molecular weights of about 378, and which may exist in equilibrium with dehydrated versions having molecular weights of about 360 (all molecular weights reported herein were derived using conventional liquid chromatography/mass spectrometry techniques). Structures I-IX and IA-IXA below illustrate various forms of these reaction products and isomers or tautomers thereof.

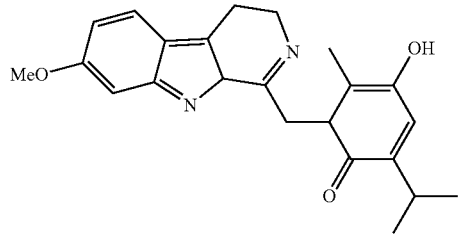

I 4-hydroxy-2-isopropyl-6-((7-methoxy-4,9a-dihydro-
3H-pyrido[3,4-b]indol-1-yl)methyl)-
5-methylcyclohexa-2,4-dien-1-one
Chemical Formula: $C_{23}H_{26}N_2O_3$
Exact Mass: 378.19

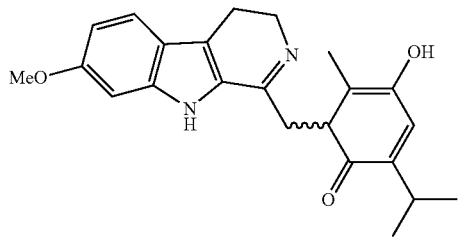

IA

Chemical Formula: $C_{23}H_{26}N_2O_3$
Exact Mass: 378.19
Molecular Weight 378.47

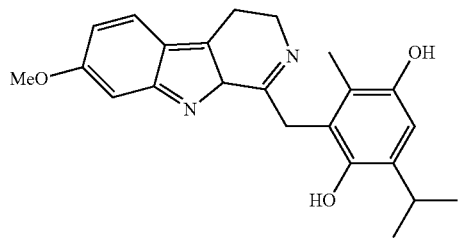

II 5-isopropyl-3-((7-methoxy-4,9a-dihydro-3H-pyrido
[3,4-b]indol-1-yl)methyl)-2-methylbenzene-1,4-diol
Chemical Formula: $C_{23}H_{26}N_2O_3$
Exact Mass: 378.19

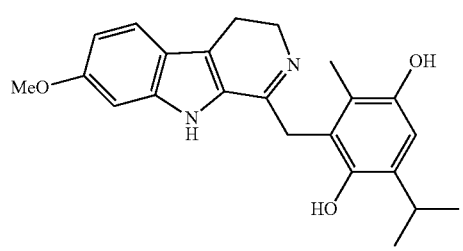

IIA

Chemical Formula: $C_{23}H_{26}N_2O_3$
Exact Mass: 378.19
Molecular Weight 378.47

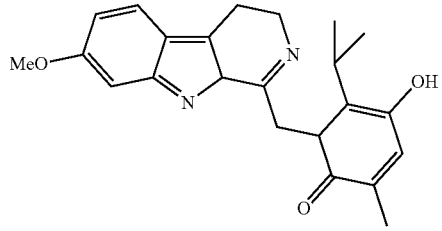

III 4-hydroxy-5-isopropyl-6-((7-methoxy-4,9a-dihydro-
3H-pyrido[3,4-b]indol-1-yl)methyl)-
2methylcyclohexa-2,4-dien-1-one
Chemical Formula: $C_{23}H_{26}N_2O_3$
Exact Mass: 378.19
Molecular Weight: 378.47

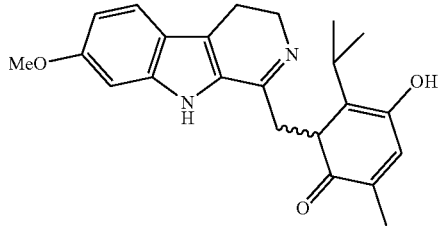

IIIA 4-hydroxy-5-isopropyl-6-((7-methoxy-4,9a-dihydro-
3H-pyrido[3,4-b]indol-1-yl)methyl)-
2methylcyclohexa-2,4-dien-1-one
Chemical Formula: $C_{23}H_{26}N_2O_3$
Exact Mass: 378.19
Molecular Weight: 378.47

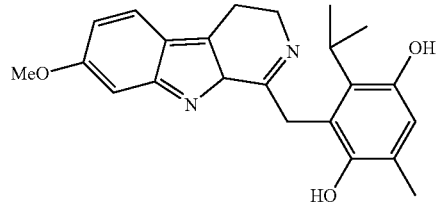

IV 2-isopropyl-3-((7-methoxy-4,9a-dihydro-
3H-pyrido[3,4-b]indol-1-yl)methyl)-
5-methylbenzene-1,4-diol
Chemical Formula: $C_{23}H_{26}N_2O_3$
Exact Mass: 378.19

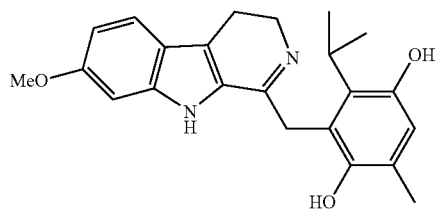

IVA

Chemical Formula: $C_{23}H_{26}N_2O_3$
Exact Mass: 378.19
Molecular Weight: 378.47

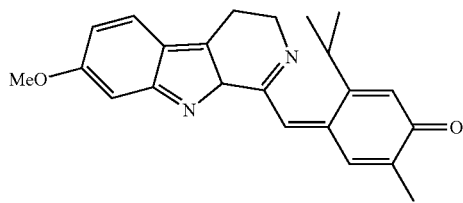

(Z)-5-isopropyl-4-((7-methoxy-4,9a-dihydro-
3H-pyrido[3,4-b]indol-1-yl)methylene)-
2-methylcyclohexa-2,5-dien-1-one
Chemical Formula: $C_{23}H_{24}N_2O_2$
Exact Mass: 360.18

V

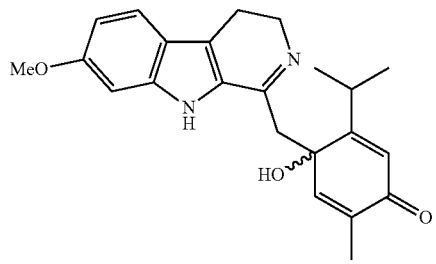

Chemical Formula: $C_{23}H_{24}N_2O_3$
Molecular Weight: 378.47

VAI

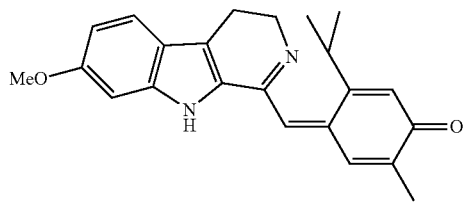

Chemical Formula: $C_{23}H_{24}N_2O_2$
Exact Mass: 360.18
Molecular Weight 360.46

VAII

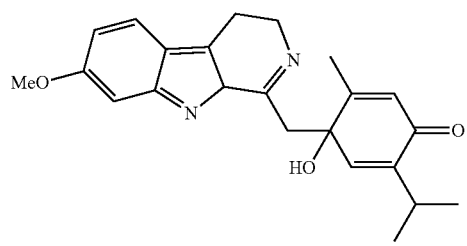

4-hydroxy-2-isopropyl-4-((7-methoxy-
4,9a-dihydro-3H-pyrido[3,4-b]indol-1-yl)methyl)-
5-methylcyclohexa-2,5-dien-1-one
Chemical Formula: $C_{23}H_{26}N_2O_3$
Exact Mass: 378.19

VI

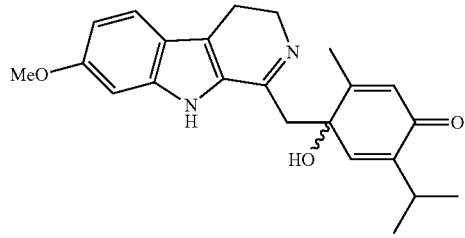

Chemical Formula: $C_{23}H_{26}N_2O_3$
Exact Mass: 378.19
Molecular Weight 378.47

VIA

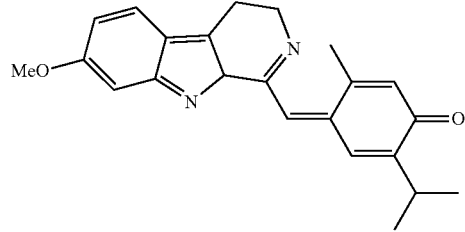

(Z)-2-isopropyl-4-((7-methoxy-4,9a-dihydro-
3H-pyrido[3,4-b]indol-1-yl)methylene)-
5-methylcyclohexa-2,5-dien-1-one
Chemical Formula: $C_{23}H_{24}N_2O_2$
Exact Mass: 360.18

VII

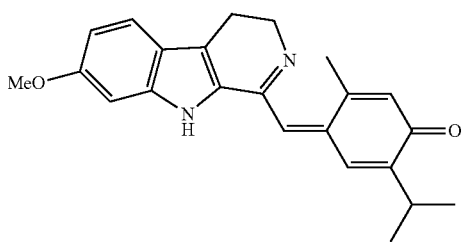

Chemical Formula: $C_{23}H_{24}N_2O_2$
Exact Mass: 360.18
Molecular Weight 360.46

VIIA

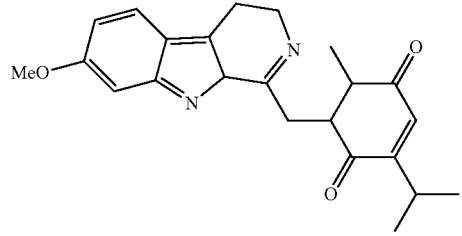

2-isopropyl-6-((7-methoxy-4,9a-dihydro-
3H-pyrido[3,4-b]indol-1-yl)methyl)-
5-methylcyclohex-2-ene-1,4-dione
Chemical Formula: $C_{23}H_{26}N_2O_3$
Exact Mass: 378.19

VIII

-continued

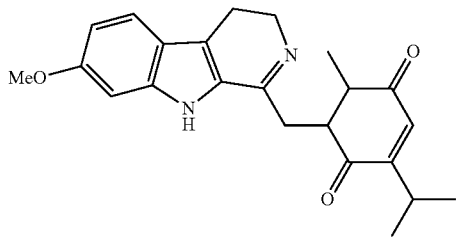

VIIIA

Chemical Formula: $C_{23}H_{26}N_2O_3$
Exact Mass: 378.19
Molecular Weight 378.47

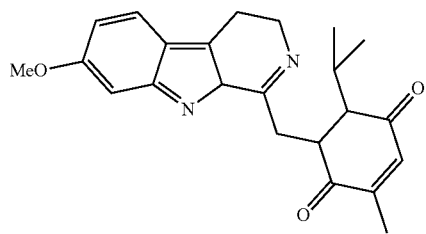

IX 5-isopropyl-6-((7-methoxy-4,9a-dihydro-
3H-pyrido[3,4-b]indol-1-yl)methyl)-
2-methylcyclohex-2-ene-1,4-dione
Chemical Formula: $C_{23}H_{26}N_2O_3$
Exact Mass: 378.19
Molecular Weight: 378.47

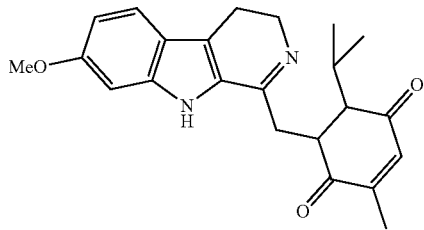

IXA

Chemical Formula: $C_{23}H_{26}N_2O_3$
Exact Mass: 378.19
Molecular Weight: 378.47

In the foregoing, structures, the wavy bond indicates possible stereo isomers. Moreover, the orientation of the thymoquinone moiety is not limited as depicted above. For example, it will be appreciated that structure IIIA above also encompasses:

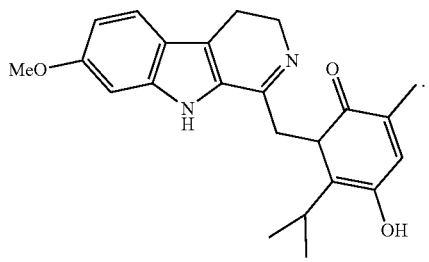 [SMILES: COc1ccc2c3c([nH]c2c1)C(CC1C(=O)C(C)=CC(O)=C1C(C)C)=NCC3]

Likewise, structure IVA encompasses:

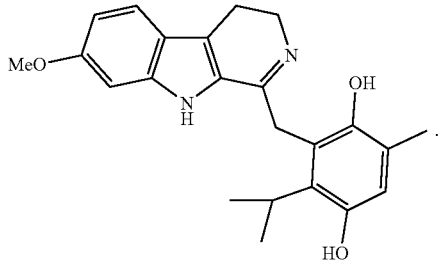 [SMILES: COc1ccc2c3c([nH]c2c1)C(Cc1c(O)c(C)cc(O)c1C(C)C)=NCC3]

Likewise, structures VAI and VAII encompass:

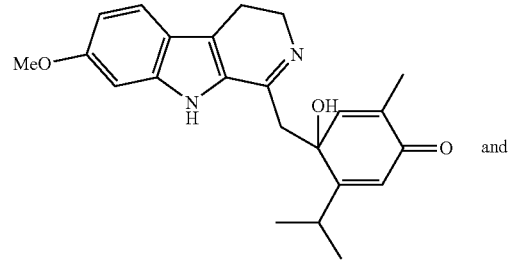

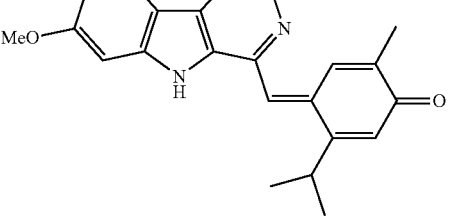

respectively.

Figure 12:
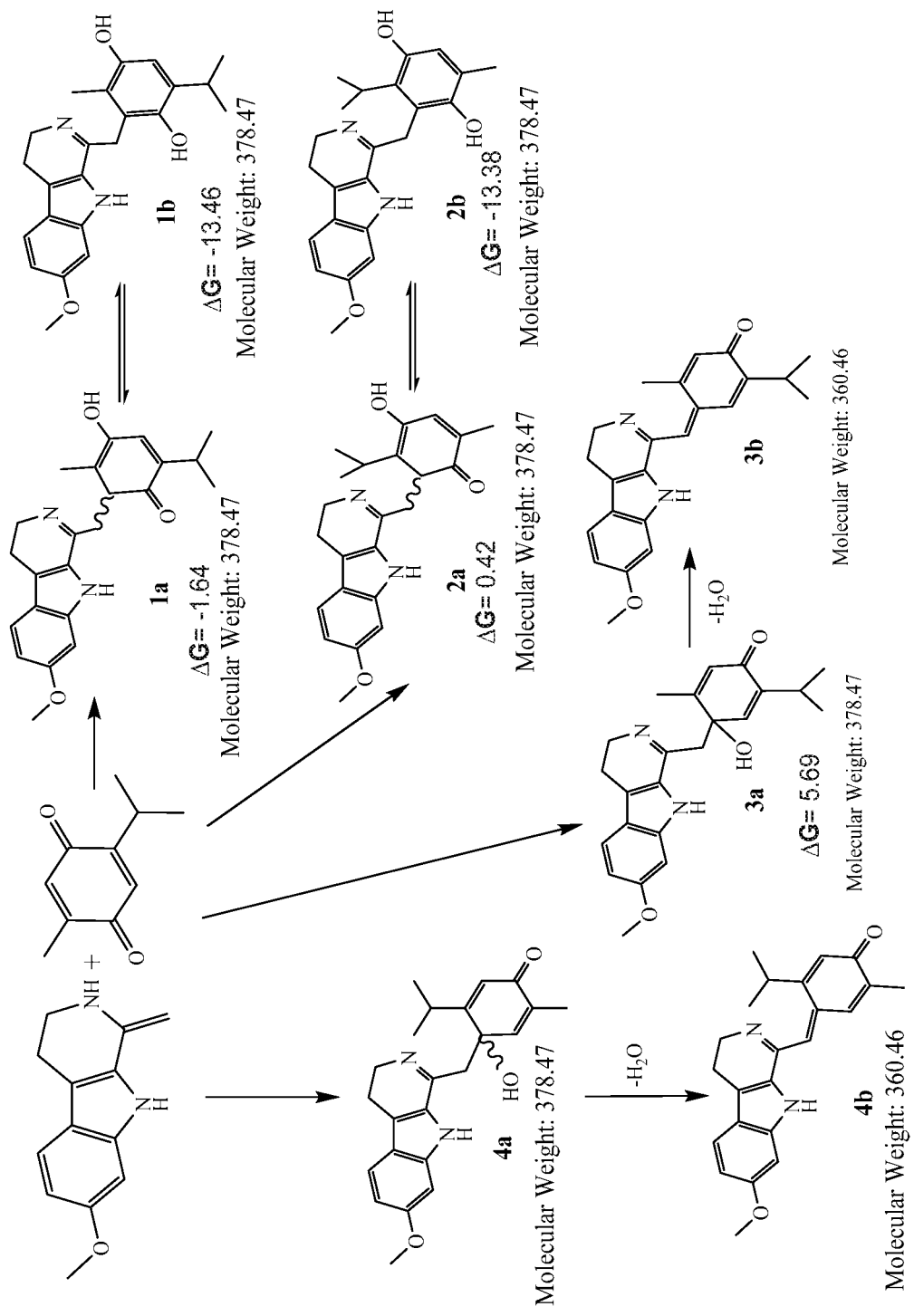
FIG. 12 shows reaction schemes giving rise to favored tautomers GZ 725-360 and GZ 725-378, their molecular structures, and Gibbs Free Energy Change, ΔG in kcal/mol from Density Functional Theory Calculations.

It will also be appreciated that double bonds are delocalized in aromatic structures. Thus, it is understood that the present disclosure should be construed to cover all resonance structures unless compounds can be isolated individually. The above reaction products are characterized by a single thymoquinone moiety and a single harmaline or harmaline-like moiety. These predominate during the initial stages of the reactions. In these reactions, the substituent of the pyridyl ring of harmaline reacts at an unsubstituted carbon atom which is alpha to either of the carbonyl groups of TQ. This phenomenon is illustrated in Structures I-IV and IA-VIA above. In another reaction scheme, the substituent of the pyridyl ring of harmaline reacts directly with either of the carbonyl groups of TQ. These types of reactions are illustrated in Structures V-VII and VA-VIIA above. As illustrated in FIG. 12, Harmaline exhibits enamine like structure in solvents like methanol (as shown above). When Harmaline is dissolved in a solvent along with thymoquinone, it undergoes enamine addition reaction at the C3 carbon of thymoquinone to furnish both structures 1a, 1b at C6 carbon to furnish both structures 2a and 2b. The similar reaction can also takes place at C1 and C4 carbonyl carbon to furnish structures 3a, 3b, 4a and 4b.

The thermodynamic properties of the harmaline and TQ reactants and reaction products (isomers of ~MW 378) were used to obtain reaction energetics using Density Functional Theory (DFT). Additional calculations were used to determine enthalpy, entropy, and Gibbs free energy values for the reactions. Reaction products II and IV were found to be the most thermodynamically favorable and smaller free energy values. Reaction product II was deemed to be the most stable and had the lowest free energy value. Note that compounds II and IV are characterized by reaction of the pyridyl ring methyl substituent with one of the two unsubstituted carbon atoms alpha to a corresponding carbonyl carbon, and two hydroxyl substituents on the TQ ring.

However, if the reaction mixtures are allowed to set for an extended period of time, e.g., from about 3-30 days, other reaction products having higher molecular weights of about 542, or in oxidized forms, about 540 are formed as the predominant reaction product. These reaction products are characterized by the presence of two thymoquinone moieties and a single harmaline or harmaline-like moiety. These same types of higher molecular weight species can be obtained if, after the initial reaction to yield the 378/360 MW products I-VII, the reaction mixtures are refluxed for a period of from about 30-120 minutes.

In particular, the MW 542 reaction products, and their oxidized MW 540 reaction products, formed by the reaction between thymoquinone and harmaline are set forth below as compounds XA-XF:

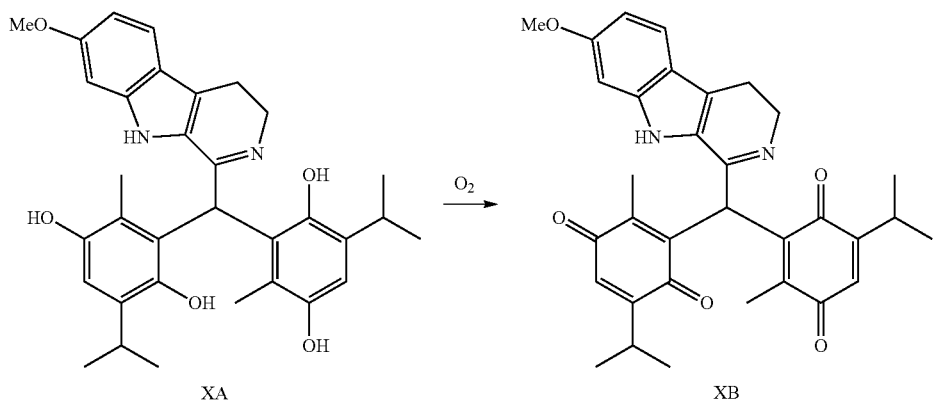

3,3'-((7-methoxy-4,9-dihydro-3H-pyrido[3,4-b]indol-1-yl)methylene)bis(5-isopropyl-2-methylbenzene-1,4-diol)
Chemical Formula: $C_{33}H_{38}N_2O_5$
Exact Mass: 542.28
Molecular Weight: 542.68
3,3'-((7-methoxy-4,9-dihydro-3H-pyrido[3,4-b]indol-1-yl)methylene)bis(5-isopropyl-2-methylcyclohexa-2,5-diene-1,4-dione)
Chemical Formula: $C_{33}H_{34}N_2O_5$
Exact Mass: 538.25
Molecular Weight: 538.64

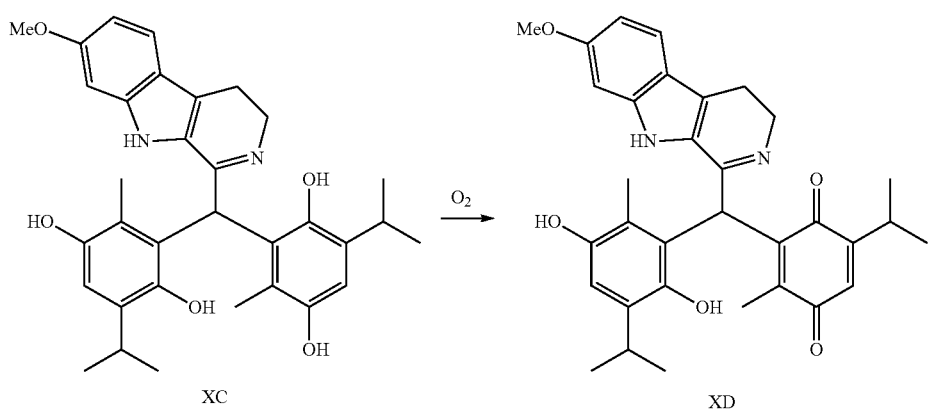

XC
3,3'-((7-methoxy-4,9-dihydro-3H-pyrido[3,4-b]indol-1-yl)methylene)bis
(5-isopropyl-2-methylbenzene-1,4-diol)
Chemical Formula: $C_{33}H_{38}N_2O_5$
Exact Mass: 542.28
Molecular Weight: 542.68

XD
3-((2,5-dihydroxy-3-isopropyl-6-methylphenyl)
(7-methoxy-4,9-dihydro-3H-pyrido[3,4-b]indol-1-yl)
methyl)-5-isopropyl-2-
methylcyclohexa-2,5-diene-1,4-dione
Chemical Formula: $C_{33}H_{36}N_2O_5$
Exact Mass: 540.26
Molecular Weight: 540.66

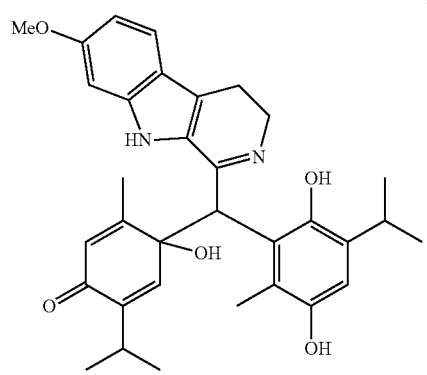

XE
4-((2,5-dihydroxy-3-isopropyl-6-methylphenyl)
(7-methoxy-4,9-dihydro-3H-pyrido
[3,4-b]indol-1-yl)methyl)-4-hydroxy-2-isopropyl-
5-methylcyclohexa-2,5-dien-1-one
Chemical Formula: $C_{33}H_{38}N_2O_5$
Exact Mass: 542.28
Molecular Weight: 542.68

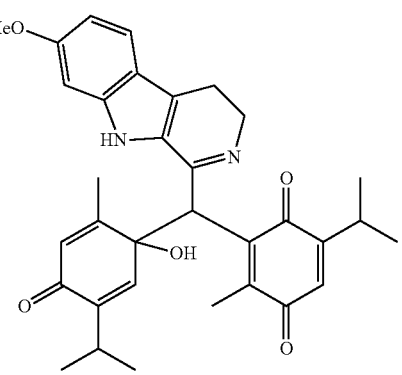

XF
3-((1-hydroxy-5-isopropyl-2-methyl-4-
oxocyclohexa-2,5-dien-1-yl)(7-methoxy-4,9-dihydro-
3H-pyrido[3,4-b]indol-1-yl)methyl)-
5-isopropyl-2-methylcyclohexa-2,5-diene-1,4-dione
Chemical Formula: $C_{33}H_{36}N_2O_5$
Exact Mass: 540.26
Molecular Weight: 540.66

Presently, compounds IIA and VIIA above are deemed to be the most active, particularly in the context of diabetes. Particularly preferred compounds are selected from the group consisting of compounds IA, IIA, IIIA, IVA, VIA, and VIIA, and the isomers and tautomers thereof.

The present invention provides compositions which may be used as improved chemotherapeutics for treatment of humans, and especially for treatment of human cancers and diabetes, and corresponding methods for preparing such compositions and use thereof. Generally speaking, the chemotherapeutics of the invention are in the form of reaction products of TQ with harmaline and related compounds, and the derivatives, solvates, prodrugs, isomers, and tautomers thereof. The reaction products can be directly used, or can be modified or derivatized to provide therapeutically effective and pharmaceutically acceptable esters, metal complexes (e.g., Cu, Fe, Zn, Pt, V), and salts.

The invention also provides new methods for treatment of cancers and diabetes (both Type I and Type II) by administration of appropriate quantities of the reaction product compositions hereof. Hence, the compositions are particularly designed for use in the treatment of cancers and diabetes, and the compositions can be used for the manufacture of medicaments for anti-cancer and anti-diabetes therapeutic applications. In addition, the invention provides compositions for the treatment of cancers and diabetes comprising administering therapeutically effective amounts of the new compositions, prepared by processes known per se, with a pharmaceutically acceptable carrier.

A "chemotherapeutic," "chemotherapeutic agent," or simply "therapeutic agent," as used herein refers to one or more of the reaction products of TQ and harmaline described herein as useful in the treatment of human conditions, especially human cancers and diabetes. Chemotherapeutics may be cytostatic, selectively toxic or destructive of cancerous tissue and/or cells, including cancer stem cells, but also include indiscriminately cytotoxic compounds used in cancer treatments.

The therapeutic agents of the invention are used in therapeutically effective amounts, i.e., amounts that will elicit the biological or medical response of a tissue, system, or subject that is being sought, and in particular to elicit some desired therapeutic effect against a variety of human diseases, and especially cancers and diabetes; in the case of cancers, the agents operate by preventing and/or inhibiting proliferation and/or survival of cancerous cells, including cancer stem cells, and/or by slowing the progression of cancers. Those skilled in the art recognize that an amount may be considered therapeutically effective even if the condition is not totally eradicated or prevented, but it or its symptoms and/or effects are improved or alleviated partially in the subject. Of course, the appropriate makeup of the agents hereof and dosing regimens using such agents will depend on the particular cancer or diabetes being treated, the extent of the disease, and other factors related to the patient as determined by those skilled in the art. Hence, the terms "therapeutic" or "treat," as used herein, refer to products or processes in accordance with the invention that are intended to produce a beneficial change in an existing condition (e.g., cancerous tissue, tumor size, metastases, etc., and the amelioration of diabetes symptoms) of a subject, such as by reducing the severity of the clinical symptoms and/or effects of the condition, and/or reducing the duration of the symptoms/effects of a subject.

Additional ingredients may be included with the chemotherapeutic agents of the invention for administration to the subject. Such additional ingredients include, other active agents, preservatives, buffering agents, salts, carriers, excipients, diluents, or other pharmaceutically-acceptable ingredients. The active agents that could be included in the compositions include antiviral, antibiotic, or other anticancer compounds; the latter could include the compounds described in PCT publication serial number WO2016/064676, such as curcumin, harmine, and isovanillin, and metabolites, derivatives, isomers, tautomers, esters, complexes and salts of any of the foregoing.

The therapeutic agents of the invention give significant and unexpected therapeutic results, particularly in the context of anti-cancer and anti-diabetes results. In use, a therapeutically effective amount of an agent or composition in accordance with the invention is administered to a subject in need thereof. Such may comprise a single unit dosage or, more usually, periodic (e.g., daily) administration of lower dosages over time.

The dosages may be administered in any convenient manner, such as by oral, rectal, nasal, ophthalmic, parenteral (including intraperitoneal, gastrointestinal, intrathecal, intravenous, cutaneous or topical (e.g., dermal patch), subcutaneous (e.g., injection or implant), or intramuscular) administrations. The dosage forms of the invention may be in the form of liquids, gels, suspensions, ointments, solutions, or solids (e.g., powders, tablets, pills, or capsules). Moreover, therapeutically effective amounts of the agents of the invention may be co-administered with other chemotherapeutic agent(s), where the two products are administered substantially simultaneously or in any sequential manner.

Levels of dosing using the compositions of the invention are quite variable owing to factors such as the patient's age, patient's physical condition, the type of condition(s) being treated (e.g., specific cancer(s) or diabetes), and the severity of the conditions. In general, however, regardless of the dosage form or route of administration employed, such as liquid solutions or suspensions, capsules, pills, or tablets, via oral, parenteral, or injection, the compositions should be dosed of from about 5 to 2000 mg per day, and more usually from about 100-800 mg per day. Such dosages may be based on a single administration per day, but more usually multiple administrations per day.

As used herein, the phrase "and/or," when used in a list of two or more items, means that any one of the listed items can be employed by itself or any combination of two or more of the listed items can be employed. For example, if a composition is described as containing or excluding components A, B, and/or C, the composition can contain or exclude A alone; B alone; C alone; A and B in combination; A and C in combination; B and C in combination; or A, B, and C in combination.

The present description also uses numerical ranges to quantify certain parameters relating to various embodiments of the invention. It should be understood that when numerical ranges are provided, such ranges are to be construed as providing literal support for claim limitations that only recite the lower value of the range as well as claim limitations that only recite the upper value of the range. For example, a disclosed numerical range of about 10 to about 100 provides literal support for a claim reciting "greater than about 10" (with no upper bounds) and a claim reciting "less than about 100" (with no lower bounds).

As used herein, pharmaceutically acceptable salts with reference to the reaction products of the present invention mean salts of the reaction products which are pharmaceutically acceptable, i.e., salts which are useful in preparing pharmaceutical compositions that are generally safe, non-toxic, and neither biologically nor otherwise undesirable and are acceptable for human pharmaceutical use, and which possess the desired degree of pharmacological activity. Such pharmaceutically acceptable salts include acid addition salts formed with inorganic acids such as hydrochloric acid, hydrobromic acid, sulfuric acid, nitric acid, phosphoric acid, and the like; or with organic acids such as 1,2-ethanedisulfonic acid, 2-hydroxyethanesulfonic acid, 2-naphthalenesulfonic acid, 3-phenylpropionic acid, 4,4'-methylenebis(3-hydroxy-2-ene-1-carboxylic acid), 4-methylbicyclo[2.2.2]oct-2-ene-1-carboxylic acid, acetic acid, aliphatic mono- and dicarboxylic acids, aliphatic sulfuric acids, aromatic sulfuric acids, benzenesulfonic acid, benzoic acid, camphorsulfonic acid, carbonic acid, cinnamic acid, citric acid, cyclopentanepropionic acid, ethanesulfonic acid, fumaric acid, glucoheptonic acid, gluconic acid, glutamic acid, glycolic acid, heptanoic acid, hexanoic acid, hydroxynaphthoic acid, lactic acid, laurylsulfuric acid, maleic acid, malic acid, malonic acid, mandelic acid, methanesulfonic acid, muconic acid, o-(4-hydroxybenzoyl)benzoic acid, oxalic acid, p-chlorobenzenesulfonic acid, phenyl-substituted alkanoic acids, propionic acid, p-toluenesulfonic acid, pyruvic acid, salicylic acid, stearic acid, succinic acid, tartaric acid, tertiarybutylacetic acid, trimethylacetic acid, and the like. Pharmaceutically acceptable salts also include base addition salts which may be formed when acidic protons present are capable of reacting with inorganic or organic bases. Acceptable inorganic bases include sodium hydroxide, sodium carbonate, potassium hydroxide, aluminum hydroxide and calcium hydroxide. Acceptable organic bases include ethanolamine, diethanolamine, triethanolamine, tromethamine, N-methylglucamine and the like. It should be recognized that the particular anion or cation forming a part of any salt of this invention is not critical, so long as the salt, as a whole, is pharmacologically acceptable. Additional examples of pharmaceutically acceptable salts and their methods of preparation and use are presented in Handbook of Pharmaceutical Salts Properties, and Use, P. H. Stahl & C. G. Wermuth eds., ISBN 978-3-90639-058-1 (2008).

In preparing the reaction product compositions of the invention, use should be made of ingredients of relatively high purity, typically at least about 90% by weight pure, and more preferably at least about 98% by weight pure. The use of naturally occurring sources for the ingredients is generally not appropriate or desirable, because these naturally occurring products contain relatively small amounts of the desired components and/or have potentially interfering compounds therein. Use of low-purity ingredients often leads to little or no reaction products in accordance with the invention.

Thus, the preferred starting compounds or components of the invention are either synthetically derived or derived from one or more naturally occurring product(s) which have been significantly modified so as to contain at least about 90% by weight (more preferably at least about 98% by weight) of the desired component. As used herein, "synthetically derived" means that the component in question was synthesized using specific starting ingredients and one or more chemical and/or biological reactions to obtain substantially pure compounds. Modification of naturally occurring products may involve extractions, or any other physical or chemical steps to achieve the desired end product.

EXAMPLES

The following examples set forth methods in accordance with the invention. It is to be understood, however, that these examples are provided by way of illustration and nothing therein should be taken as a limitation upon the overall scope of the invention.

Examples

A series of low temperature thymoquinone/harmaline syntheses were undertaken to determine the principal products synthesized by molecular weight, and the quantity thereof as compared with byproducts. Generally speaking, each test involved dissolving respective quantities of thymoquinone and harmaline in absolute ethanol at different ratios, allowing the reaction to occur at different low temperature levels, and then analyzing the reaction products with a G2XS Liquid Chromatography-Mass Spectrometry (LCMS). Specifically, use was made of a Waters G2XS LCMS system with ACQUITY UPLC BEH C18 Column, 130 Å, 1.7 µm, 2.1 mm×100 mm, under the below-listed conditions. The "mass" referred to in the examples is the molecular weight of the products as derived from the LCMS. A spectrum from each test is set forth in the drawings.

Example 1: 1:2 −80° C.

A. Ingredients
  164 mg thymoquinone
  107 mg harmaline
  2 mL EtOH
B. Reaction Conditions
  1. Combine thymoquinone, harmaline, and ethanol
  2. Mix until dissolved
  3. Put in −80° C. freezer over the weekend (~72 hours)
  4. Remove from freezer and allow sample to return to room temperature
  5. Add 5 µL of sample to 1 mL of EtOH, with mixing
  6. Add 10 µL of dilution to 0.75 mL LCMS grade water and 0.25 mL of LCMS grade acetonitrile LCMS column gradient:
Solvent A Water with 1% Formic Acid
Solvent B Acetonitrile with 1% Formic Acid

| Time (min) | Flow (mL/min) | % A | % B |
|---|---|---|---|
| 0 | 0.7 | 80 | 20 |
| 9 | 0.7 | 2 | 98 |
| 10 | 0.7 | 2 | 98 |
| 12 | 0.7 | 80 | 20 |

FIG. 1 is the spectrum generated in this example. The following table lists the retention times, the areas under the important peaks, the % areas, and the mass of the corresponding reaction products.

| Retention Time (min) | Area | % Area | Mass |
|---|---|---|---|
| 0.58 | 36621729 | 25.50 | 214 |
| 1.33 | 6893008 | 4.80 | 378 |
| 1.42 | 19932648 | 13.88 | 378 |
| 1.54 | 29866114 | 20.80 | 378 |
| 1.64 | 5479588 | 3.82 | 378 |
| 1.76 | 18950909 | 13.20 | 360 |
| 1.84 | 16542199 | 11.52 | 376 |
| 2.68 | 4322666 | 3.01 | 524 |
| 3.06 | 4979449 | 3.47 | 522 |

With approximately 54.82% with the mass 378/376.

Example 2: 1:2 −80° C.

A. Ingredients
  164 mg thymoquinone
  107 mg harmaline
  2 mL EtOH
B. Reaction Conditions
  1. Combine thymoquinone, harmaline, and ethanol
  2. Mix until dissolved
  3. Put in −80° C. freezer over the weekend (~72 hours)
  4. Remove from freezer and allow sample to return to room temperature
  5. Add 2 mL of water
  6. Filter solids using Whatman 1 filter paper
  7. Wash with water
  8. Dry in oven at 90° C.
  9. Add 2 µg of sample to 1 mL of EtOH, with mixing
  10. Add 10 µL of dilution to 0.75 mL LCMS grade water and 0.25 mL of LCMS grade acetonitrile LCMS Column Gradient Solvent A Water with 1% Formic Acid
Solvent B Acetonitrile with 1% Formic Acid

| Time (min) | Flow (mL/min) | % A | % B |
|---|---|---|---|
| 0 | 0.7 | 80 | 20 |
| 9 | 0.7 | 2 | 98 |
| 10 | 0.7 | 2 | 98 |
| 12 | 0.7 | 80 | 20 |

Figure 2:
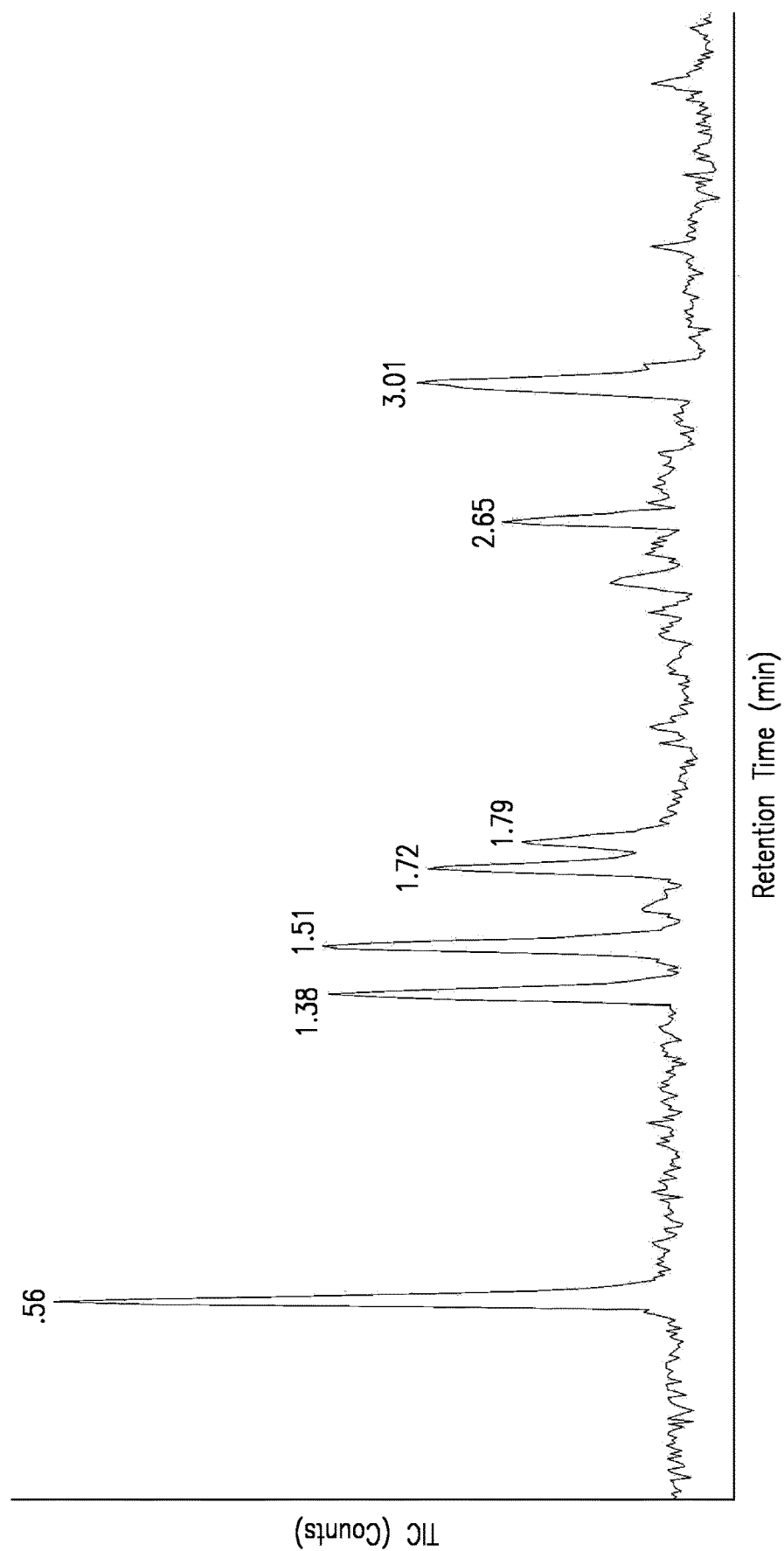
FIG. 2 is a spectrum derived from the assay described in Example 2.

FIG. 2 is the spectrum generated in this example. The following table lists the retention times, the areas under the important peaks, the % areas, and the mass of the corresponding reaction products.

| Retention Time (min) | Area | % Area | Mass |
|---|---|---|---|
| 0.56 | 30846712 | 25.93 | 214 |
| 1.38 | 18207142 | 15.30 | 378 |
| 1.51 | 20666195 | 17.37 | 378 |
| 1.72 | 12902678 | 10.84 | 360 |
| 1.79 | 8481740 | 7.13 | 358 |
| 2.65 | 7825410 | 6.58 | 524 |
| 3.01 | 20048072 | 16.85 | 522 |

With approximately 32.67% with the mass 378/3776.

Example 3: 1:3 Ratio −18° C.

A. Ingredients
  164 mg thymoquinone
  71 mg harmaline
  2 mL EtOH
B. Reaction Conditions
  1. Combine thymoquinone, harmaline, and ethanol
  2. Mix until dissolved
  3. Put in −18° C. freezer overnight
  4. Remove from freezer and allow sample to return to room temperature
  5. Add 5 µL of sample to 1 mL of EtOH, with mixing
  6. Add 10 µL of dilution to 0.75 mL LCMS grade water and 0.25 mL of LCMS grade acetonitrile LCMS Column Gradient Solvent A Water with 1% Formic Acid
Solvent B Acetonitrile with 1% Formic Acid

| Time (min) | Flow (mL/min) | % A | % B |
|---|---|---|---|
| 0 | 0.7 | 80 | 20 |
| 9 | 0.7 | 2 | 98 |
| 10 | 0.7 | 2 | 98 |
| 12 | 0.7 | 80 | 20 |

Figure 3:
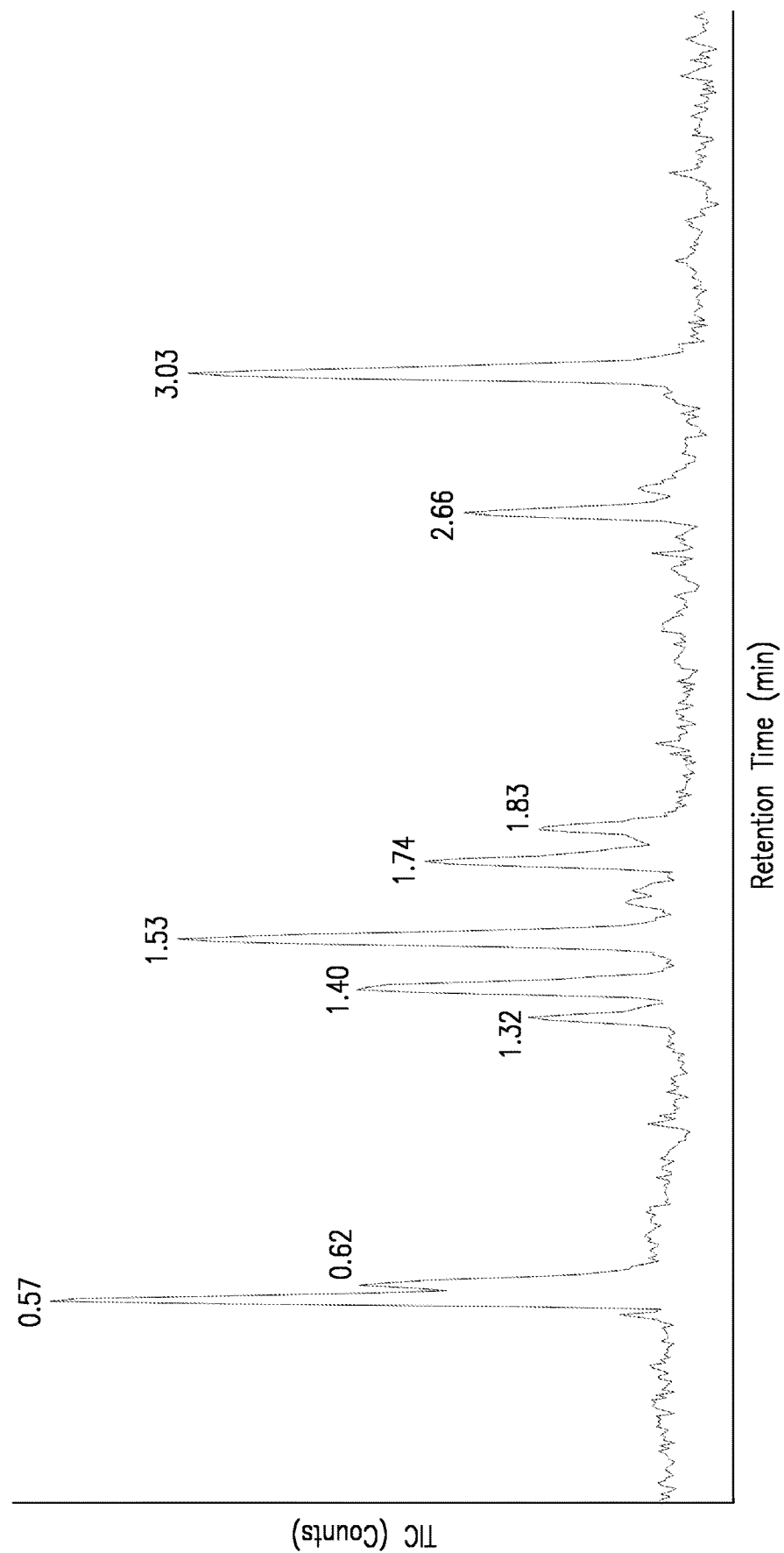
FIG. 3 is a spectrum derived from the assay described in Example 3.

FIG. 3 is the spectrum generated in this example. The following table lists the retention times, the areas under the important peaks, the % areas, and the mass of the corresponding reaction products.

| Retention Time (min) | Area | % Area | Mass |
|---|---|---|---|
| 0.57 | 29778554 | 17.69 | 214 |
| 0.61 | 17028809 | 10.12 | 212 |
| 1.32 | 6585566 | 3.91 | 378 |
| 1.4 | 20057868 | 11.92 | 378 |
| 1.53 | 31448269 | 18.68 | 378 |
| 1.74 | 14261852 | 8.47 | 360 |
| 1.83 | 8627882 | 5.13 | 376 |
| 2.66 | 10994085 | 6.53 | 524 |
| 3.03 | 29542138 | 17.55 | 522 |

With approximately 39.64% with the mass 378/376.

Example 4: 1:3 −40° C.

A. Ingredients
    164 mg thymoquinone
    71 mg harmaline
    2 mL EtOH
B. Reaction Conditions
    1. Combine thymoquinone, harmaline, and ethanol
    2. Mix until dissolved
    3. Put in −40° C. freezer overnight
    4. Remove from freezer and allow sample to return to room temperature
    5. Add 5 μL of sample to 1 mL of EtOH, with mixing
    6. Add 10 μL of dilution to 0.75 mL LCMS grade water and 0.25 mL of LCMS grade acetonitrile LCMS Column Gradient

| Solvent A Water with 1% Formic Acid | | | |
|---|---|---|---|
| Solvent B Acetonitrile with 1% Formic Acid | | | |
| Time (min) | Flow (mL/min) | % A | % B |
| 0 | 0.7 | 80 | 20 |
| 9 | 0.7 | 2 | 98 |
| 10 | 0.7 | 2 | 98 |
| 12 | 0.7 | 80 | 20 |

Figure 4:
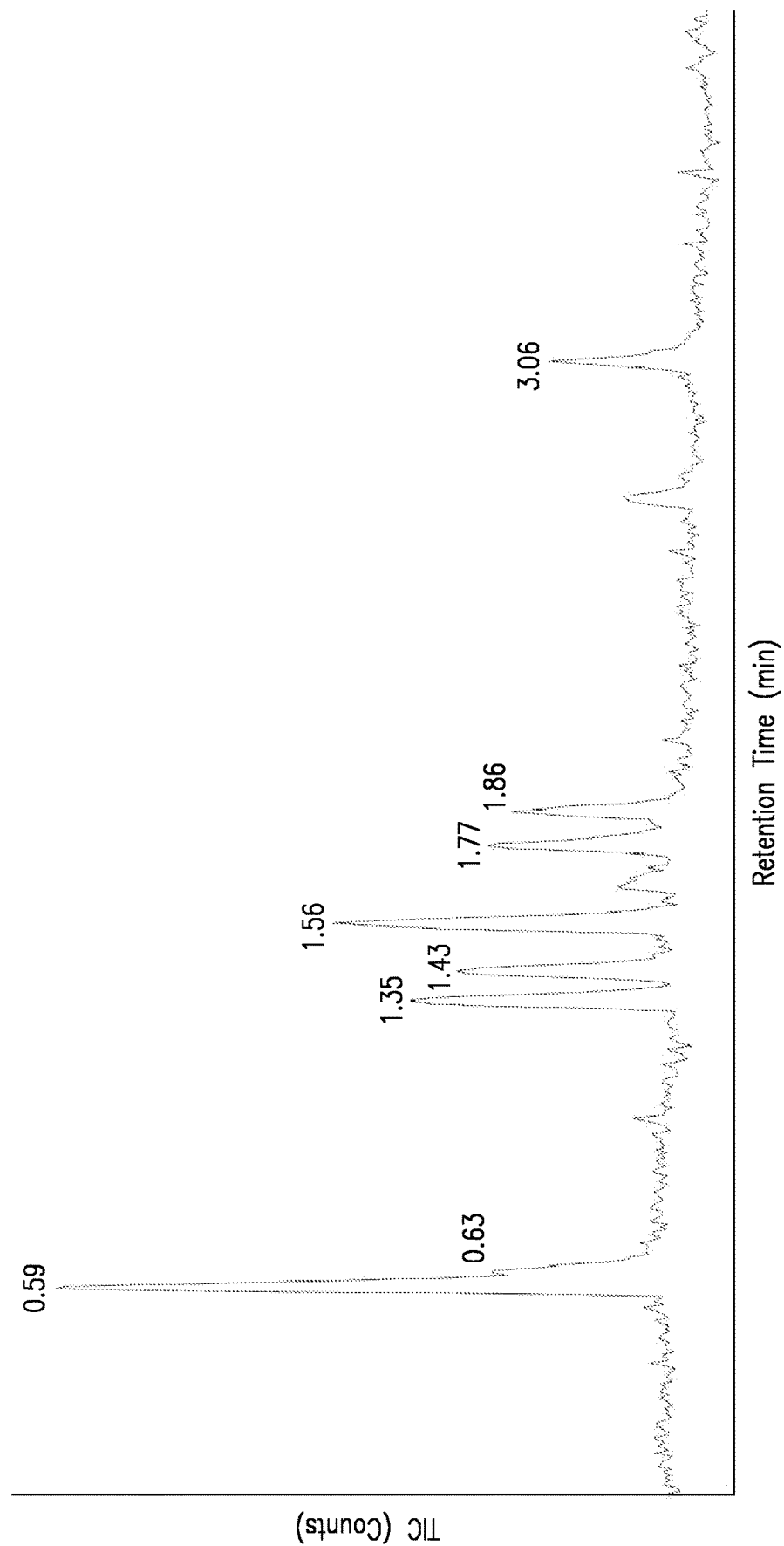
FIG. 4 is a spectrum derived from the assay described in Example 4.

FIG. 4 is the spectrum generated in this example. The following table lists the retention times, the areas under the important peaks, the % areas, and the mass of the corresponding reaction products.

| Retention Time (min) | Area | % Area | Mass |
|---|---|---|---|
| 0.59 | 40034081 | 28.57 | 214 |
| 0.63 | 9609766 | 6.86 | 212 |
| 1.35 | 18016352 | 12.86 | 378 |
| 1.43 | 13867846 | 9.90 | 378 |
| 1.56 | 24944402 | 17.80 | 378 |
| 1.77 | 13657818 | 9.75 | 360 |
| 1.86 | 11976333 | 8.55 | 376 |
| 3.06 | 8026291 | 5.73 | 522 |

With approximately 49.10% with the mass 378/376.

Example 5: 1:3 −80° C.

A. Ingredients
    164 mg thymoquinone
    71 mg harmaline
    2 mL EtOH
B. Reaction Conditions
    1. Combine thymoquinone, harmaline, and ethanol
    2. Mix until dissolved
    3. Put in −80° C. freezer over the weekend
    4. Remove from freezer and allow sample to return to room temperature
    5. Add 5 μL of sample to 1 mL of EtOH, with mixing
    6. Add 10 μL of dilution to 0.75 mL LCMS grade water and 0.25 mL of LCMS grade acetonitrile LCMS Column Gradient

| Solvent A Water with 1% Formic Acid | | | |
|---|---|---|---|
| Solvent B Acetonitrile with 1% Formic Acid | | | |
| Time (min) | Flow (mL/min) | % A | % B |
| 0 | 0.7 | 80 | 20 |
| 9 | 0.7 | 2 | 98 |
| 10 | 0.7 | 2 | 98 |
| 12 | 0.7 | 80 | 20 |

Figure 5:
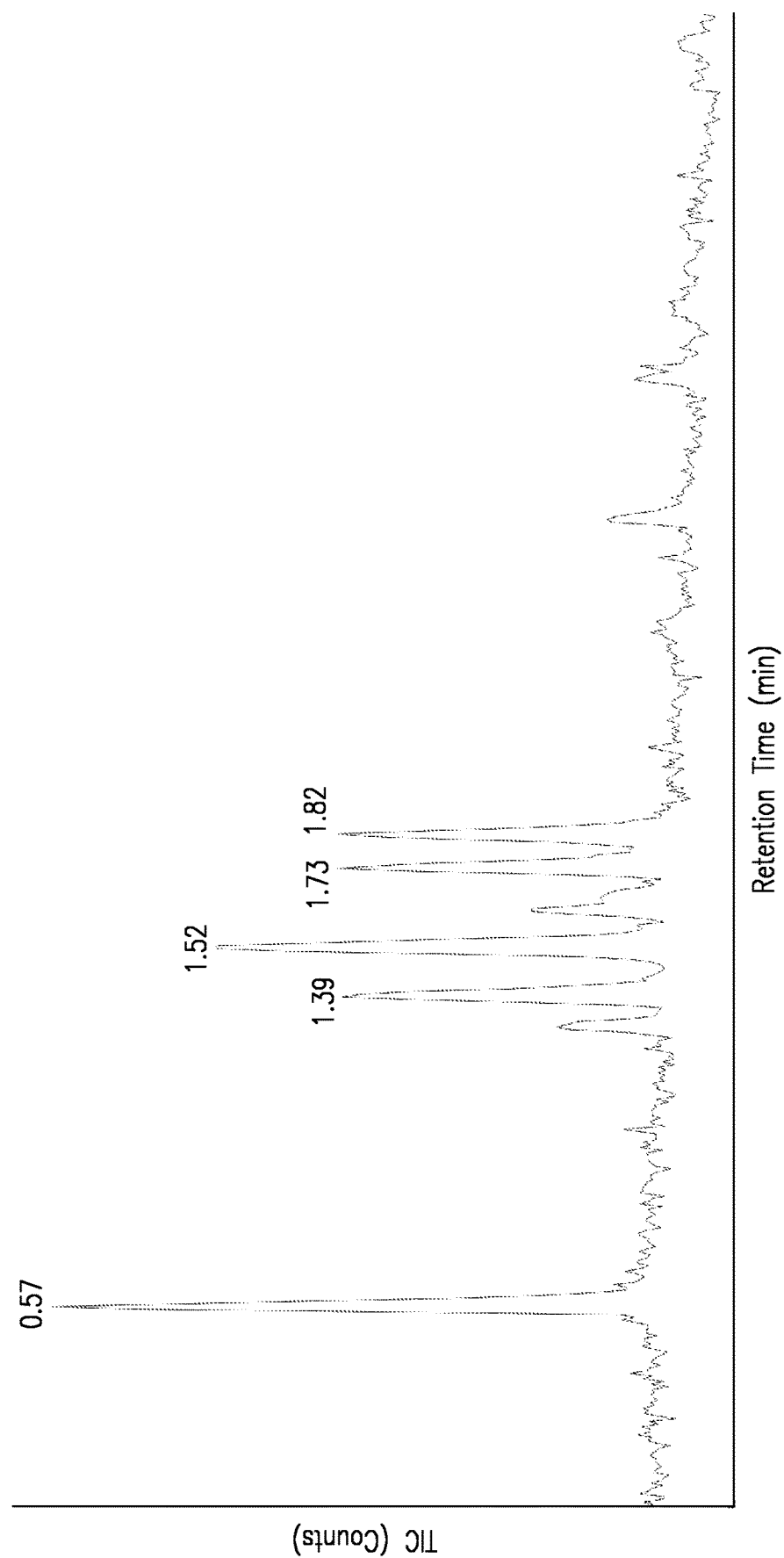
FIG. 5 is a spectrum derived from the assay described in Example 5.

FIG. 5 is the spectrum generated in this example. The following table lists the retention times, the areas under the important peaks, the % areas, and the mass of the corresponding reaction products.

| Retention Time (min) | Area | % Area | Mass |
|---|---|---|---|
| 0.57 | 25905457 | 25.81 | 214 |
| 1.39 | 17198024 | 17.14 | 378 |
| 1.52 | 24367377 | 24.28 | 378 |
| 1.73 | 16657357 | 16.60 | 360 |
| 1.82 | 16232218 | 16.17 | 376 |

With approximately 57.59% with the mass 378/376.

Example 6: 1:3 −80° C.

A. Ingredients
    164 mg thymoquinone
    71 mg harmaline
    2 mL EtOH
B. Reaction Conditions
    1. Combine thymoquinone, harmaline, and ethanol
    2. Mix until dissolved
    3. Put in −80° C. freezer over the weekend
    4. Remove from freezer and allow sample to return to room temperature
    5. Add 2 mL of water
    6. Filter using Whatman 1 filter paper
    7. Wash with water
    8. Dry in oven at 90° C.
    9. Add 2 μg of sample to 1 mL of EtOH, with mixing
    10. Add 10 μL of dilution to 0.75 mL LCMS grade water and 0.25 mL of LCMS grade acetonitrile LCMS Column Gradient

| Solvent A Water with 1% Formic Acid | | | |
|---|---|---|---|
| Solvent B Acetonitrile with 1% Formic Acid | | | |
| Time (min) | Flow (mL/min) | % A | % B |
| 0 | 0.7 | 80 | 20 |
| 9 | 0.7 | 2 | 98 |
| 10 | 0.7 | 2 | 98 |
| 12 | 0.7 | 80 | 20 |

Figure 6:
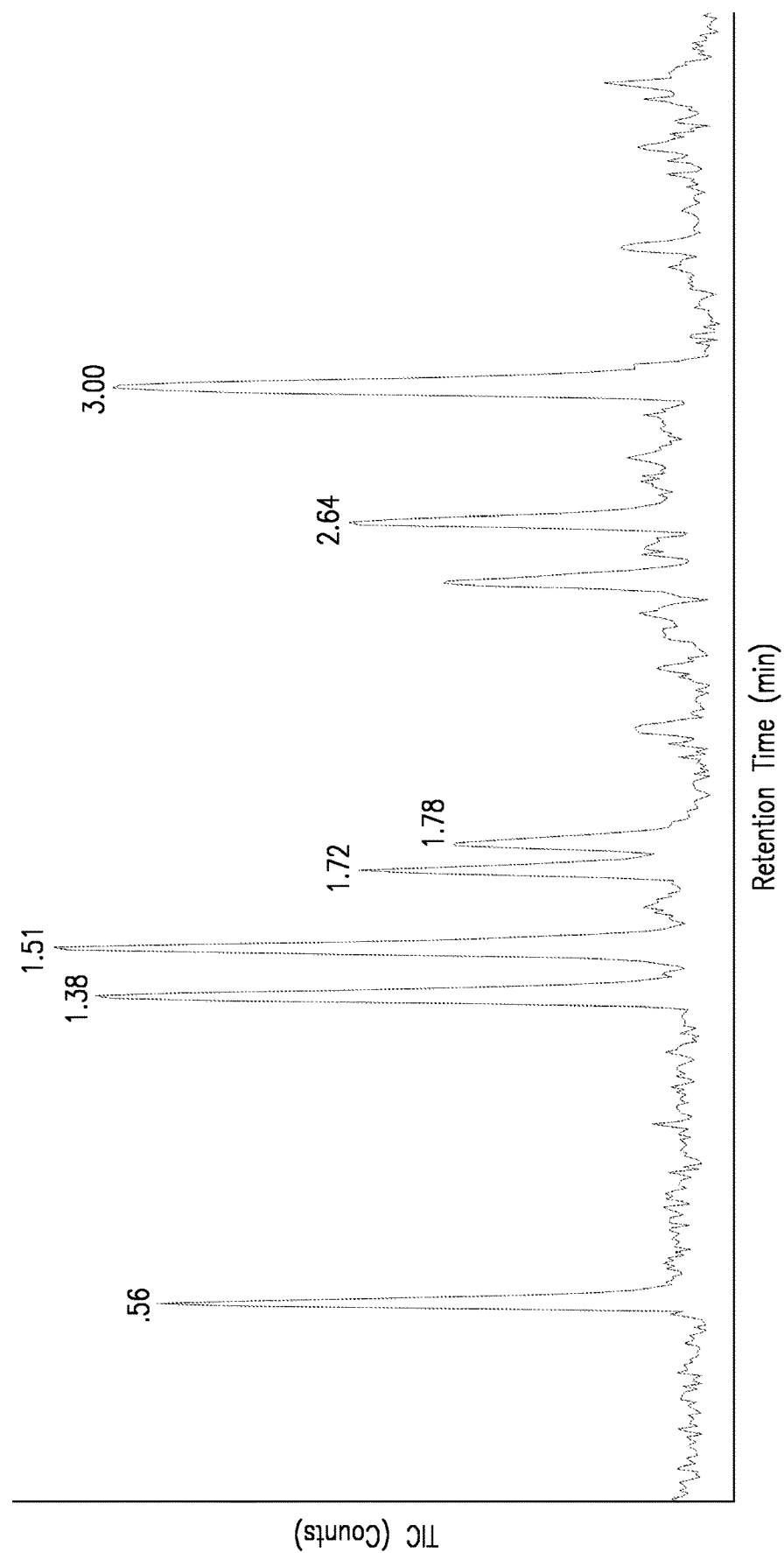
FIG. 6 is a spectrum derived from the assay described in Example 6.

FIG. 6 is the spectrum generated in this example. The following table lists the retention times, the areas under the important peaks, the % areas, and the mass of the corresponding reaction products.

| Retention Time (min) | Area | % Area | Mass |
|---|---|---|---|
| 0.56 | 20011667 | 13.93 | 214 |
| 1.38 | 25631888 | 17.84 | 378 |
| 1.51 | 27886772 | 19.41 | 378 |
| 1.72 | 12421688 | 8.65 | 360 |
| 1.78 | 10883184 | 7.58 | 358 |
| 2.64 | 13547985 | 9.43 | 524 |
| 3.00 | 33279299 | 23.16 | 520 |

With approximately 37.25% with the mass 378

Example 7: 1:4 −18° C.

A. Ingredients
 164 mg thymoquinone
 71 mg harmaline
 2 mL EtOH
B. Reaction Conditions
 1. Combine thymoquinone, harmaline, and ethanol
 2. Mix until dissolved
 3. Put in −18° C. freezer overnight
 4. Remove from freezer and allow sample to return to room temperature
 5. Add 5 μL of sample to 1 mL of EtOH, with mixing
 6. Add 10 μL of dilution to 0.75 mL LCMS grade water and 0.25 mL of LCMS grade acetonitrile LCMS Column Gradient

| Solvent A Water with 1% Formic Acid | | | |
|---|---|---|---|
| Solvent B Acetonitrile with 1% Formic Acid | | | |
| Time (min) | Flow (mL/min) | % A | % B |
| 0 | 0.7 | 80 | 20 |
| 9 | 0.7 | 2 | 98 |
| 10 | 0.7 | 2 | 98 |
| 12 | 0.7 | 80 | 20 |

Figure 7:
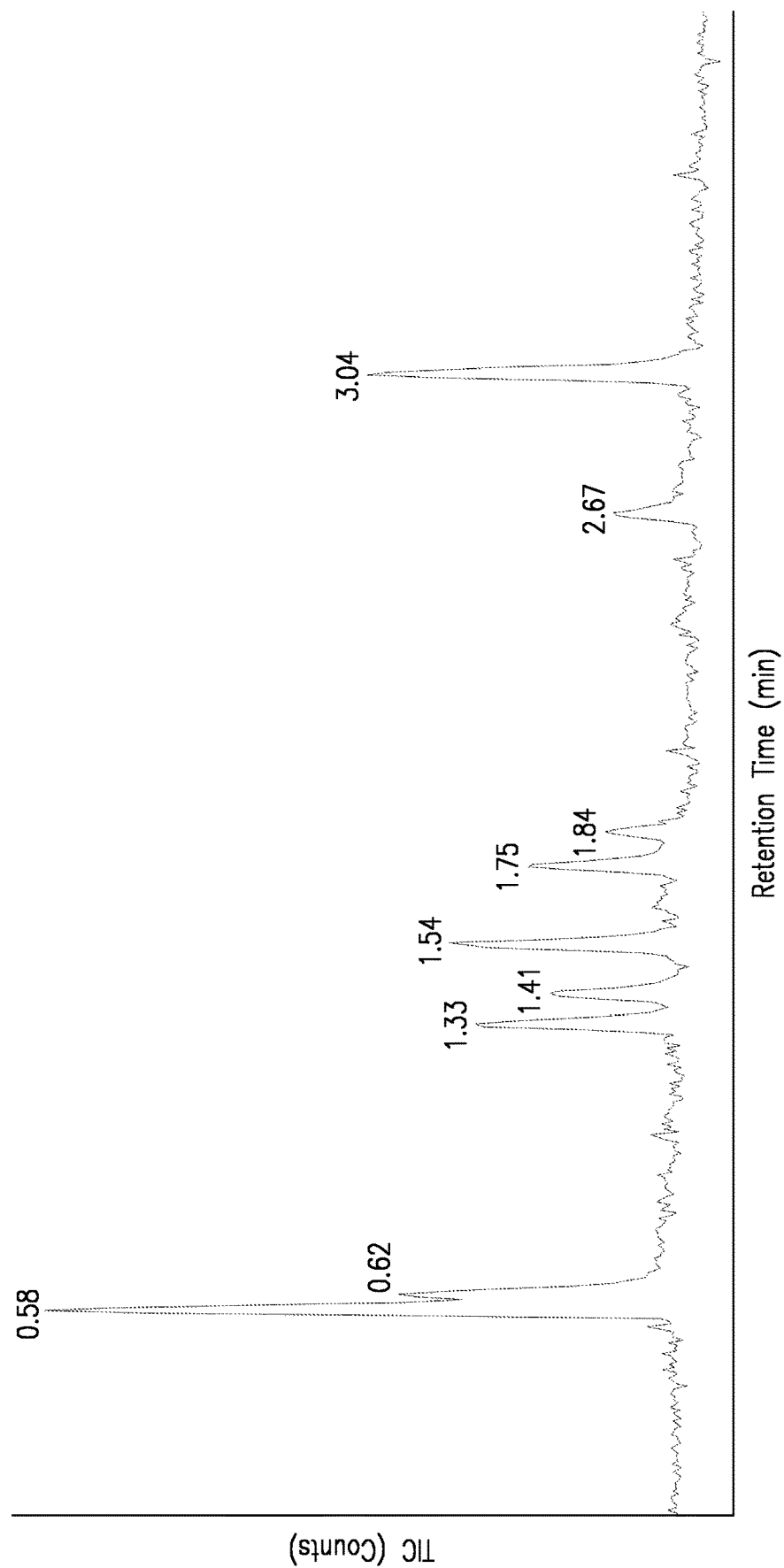
FIG. 7 is a spectrum derived from the assay described in Example 7.

FIG. 7 is the spectrum generated in this example. The following table lists the retention times, the areas under the important peaks, the % areas, and the mass of the corresponding reaction products.

| Retention Time (min) | Area | % Area | Mass |
|---|---|---|---|
| 0.58 | 33397537 | 27.90 | 214 |
| 0.62 | 15245046 | 12.73 | 212 |
| 1.33 | 11140537 | 9.31 | 378 |
| 1.41 | 7669979 | 6.41 | 378 |
| 1.54 | 14070248 | 11.75 | 378 |
| 1.75 | 9269099 | 7.74 | 360 |
| 1.84 | 3980743 | 3.33 | 376 |
| 2.67 | 3893721 | 3.25 | 524 |
| 3.04 | 21045051 | 17.58 | 522 |

With approximately 30.79% with the mass 378/376.

Example 8: 1:4 −40° C.

A. Ingredients
 164 mg thymoquinone
 71 mg harmaline
 2 mL EtOH
B. Reaction Conditions
 1. Combine thymoquinone, harmaline, and ethanol
 2. Mix until dissolved
 3. Put in −40° C. freezer overnight
 4. Remove from freezer and allow sample to return to room temperature
 5. Add 5 μL of sample to 1 mL of EtOH, with mixing
 6. Add 10 μL of dilution to 0.75 mL LCMS grade water and 0.25 mL of LCMS grade acetonitrile
 7.

LCMS Column Gradient

| Solvent A Water with 1% Formic Acid | | | |
|---|---|---|---|
| Solvent B Acetonitrile with 1% Formic Acid | | | |
| Time (min) | Flow (mL/min) | % A | % B |
| 0 | 0.7 | 80 | 20 |
| 9 | 0.7 | 2 | 98 |
| 10 | 0.7 | 2 | 98 |
| 12 | 0.7 | 80 | 20 |

Figure 8:
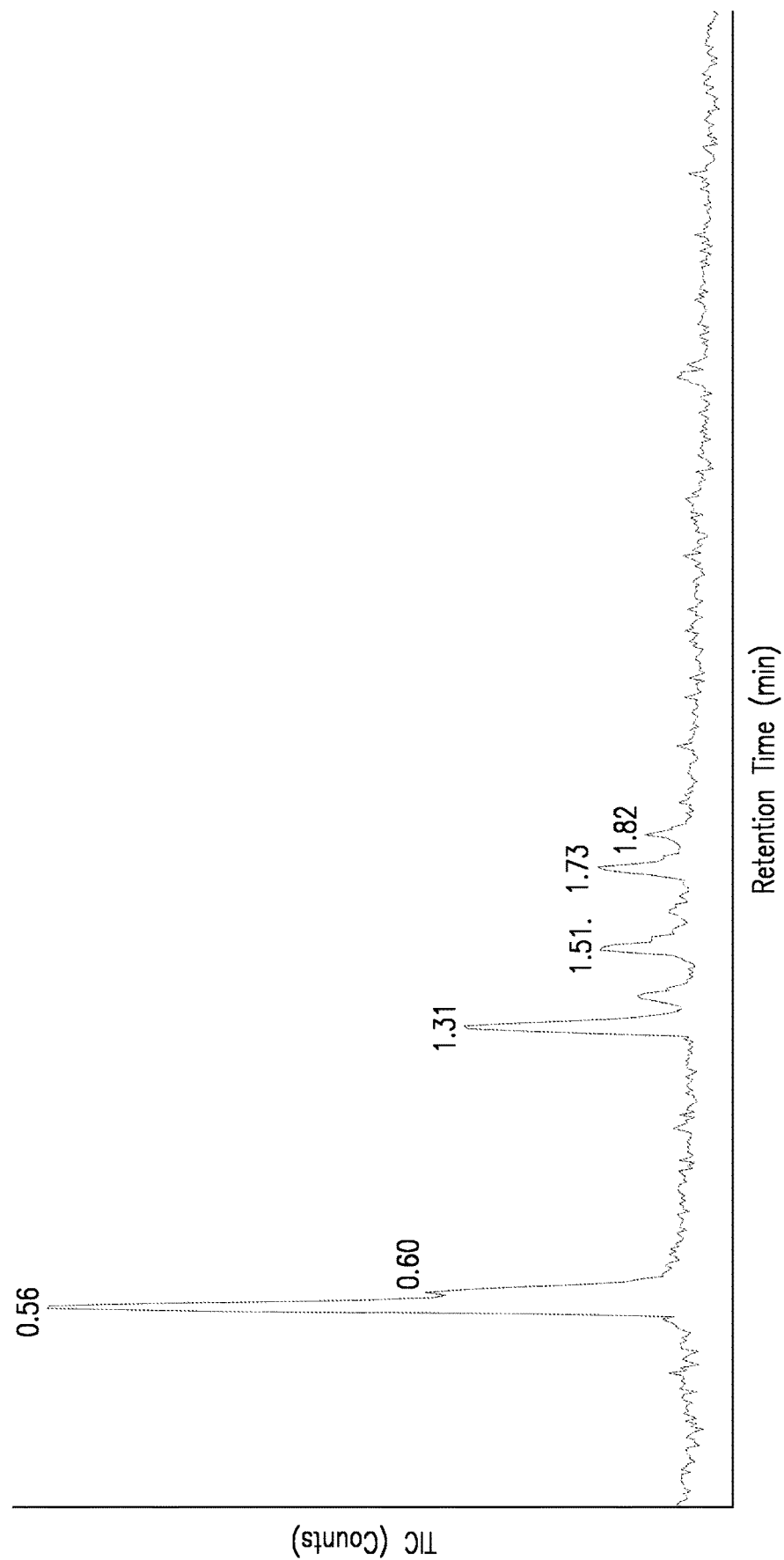
FIG. 8 is a spectrum derived from the assay described in Example 8.

FIG. 8 is the spectrum generated in this example. The following table lists the retention times, the areas under the important peaks, the % areas, and the mass of the corresponding reaction products.

| Retention Time (min) | Area | % Area | Mass |
|---|---|---|---|
| 0.56 | 45002318 | 50.26 | 214 |
| 0.6 | 12944409 | 14.46 | 212 |
| 1.31 | 15085031 | 16.85 | 378 |
| 1.51 | 7349874 | 8.21 | 378 |
| 1.73 | 6674622 | 7.45 | 360 |
| 1.82 | 2480652 | 2.77 | 376 |

With approximately 27.83% with the mass 378/376.

Example 9: 1:4 −80° C.

A. Ingredients
 164 mg thymoquinone
 54 mg harmaline
 2 mL EtOH

B. Reaction Conditions
1. Combine thymoquinone, harmaline, and ethanol.
2. Mix until dissolved
3. Put in −80° C. freezer over the weekend
4. Remove from freezer and allow sample to return to room temperature
5. Add 5 μL of sample to 1 mL of EtOH, with mixing
6. Add 10 μL of dilution to 0.75 mL LCMS grade water and 0.25 mL of LCMS grade acetonitrile LCMS Column Gradient

| Solvent A Water with 1% Formic Acid Solvent B Acetonitrile with 1% Formic Acid | | | |
|---|---|---|---|
| Time (min) | Flow (mL/min) | % A | % B |
| 0 | 0.7 | 80 | 20 |
| 9 | 0.7 | 2 | 98 |
| 10 | 0.7 | 2 | 98 |
| 12 | 0.7 | 80 | 20 |

Figure 9:
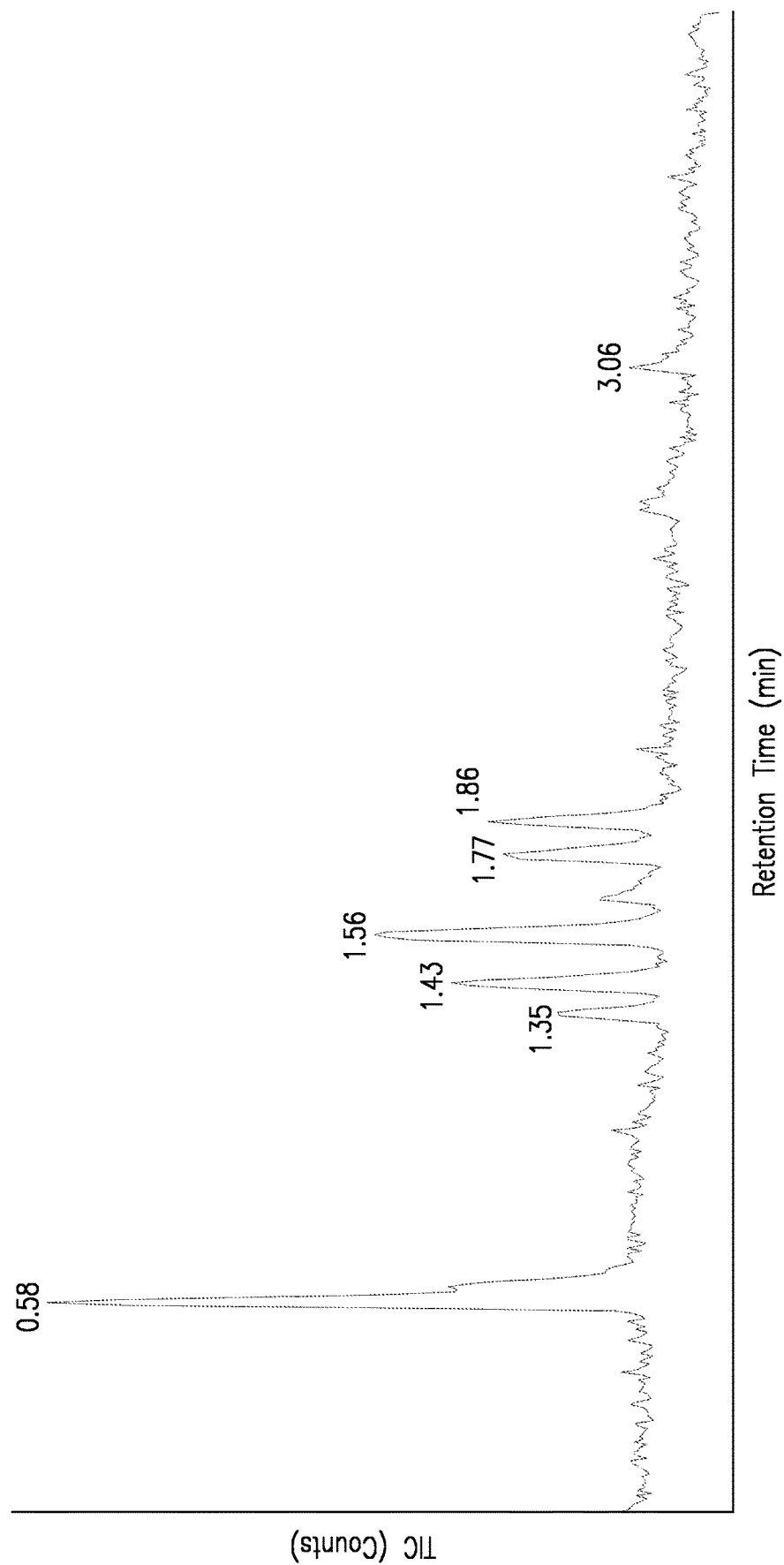
FIG. 9 is a spectrum derived from the assay described in Example 9.

FIG. 9 is the spectrum generated in this example. The following table lists the retention times, the areas under the important peaks, the % areas, and the mass of the corresponding reaction products.

| Retention Time (min) | Area | % Area | Mass |
|---|---|---|---|
| 0.58 | 48542947 | 39.91 | 214 |
| 1.35 | 7395644 | 6.08 | 378 |
| 1.43 | 15222145 | 12.51 | 378 |
| 1.56 | 22264205 | 18.30 | 378 |
| 1.77 | 11909187 | 9.79 | 360 |
| 1.86 | 11332628 | 9.32 | 376 |
| 3.06 | 4979449 | 4.09 | 524 |

With approximately 46.21% with the mass 378/376.

Example 10: 1:5 −80° C.

A. Ingredients
164 mg thymoquinone
43 mg harmaline
2 mL EtOH

B. Reaction Conditions
1. Combine thymoquinone, harmaline, and ethanol
2. Mix until dissolved
3. Put in −80° C. freezer overnight
4. Remove from freezer and allow sample to return to room temperature
5. Add 5 μL of sample to 1 mL of EtOH, with mixing
6. Add 10 μL of dilution to 0.75 mL LCMS grade water and 0.25 mL of LCMS grade acetonitrile LCMS Column Gradient

| Solvent A Water with 1% Formic Acid Solvent B Acetonitrile with 1% Formic Acid | | | |
|---|---|---|---|
| Time (min) | Flow (mL/min) | % A | % B |
| 0 | 0.7 | 80 | 20 |
| 9 | 0.7 | 2 | 98 |
| 10 | 0.7 | 2 | 98 |
| 12 | 0.7 | 80 | 20 |

Figure 10:
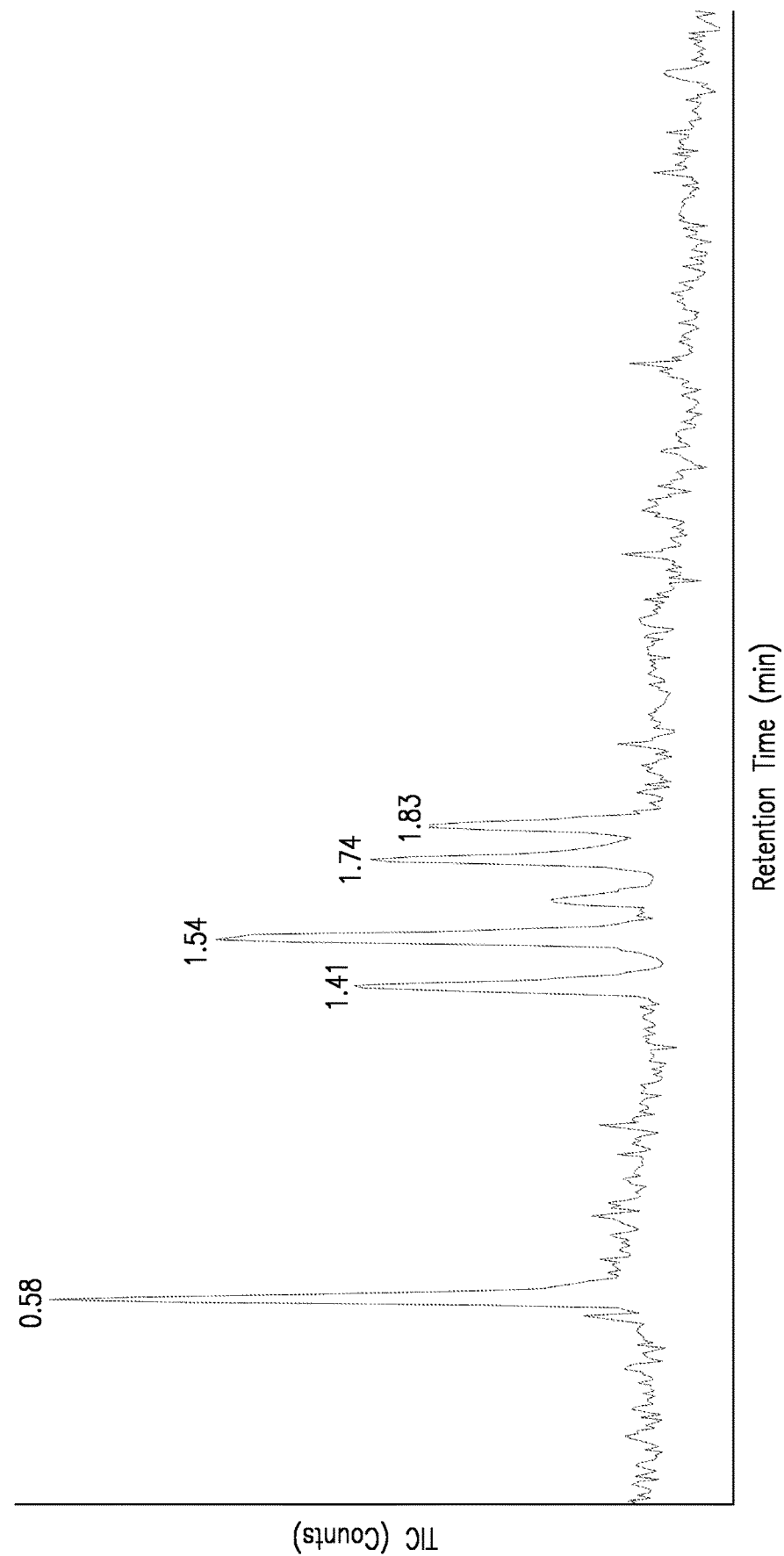
FIG. 10 is a spectrum derived from the assay described in Example 10.

FIG. 10 is the spectrum generated in this example. The following table lists the retention times, the areas under the important peaks, the % areas, and the mass of the corresponding reaction products.

| Retention Time (min) | Area | % Area | Mass |
|---|---|---|---|
| 0.58 | 16232838 | 30.34 | 214 |
| 1.41 | 9956388 | 18.61 | 378 |
| 1.54 | 16126637 | 30.14 | 378 |
| 1.74 | 10037802 | 18.76 | 360 |
| 1.83 | 1153415 | 2.16 | 376 |

With approximately 50.90% with the mass 378/376.

Example 11: 1:5 −80° C.

A. Ingredients
164 mg thymoquinone
43 mg harmaline
2 mL EtOH

B. Reaction Conditions
1. Combine thymoquinone, harmaline, and ethanol
2. Mix until dissolved
3. Put in −80° C. freezer overnight
4. Remove from freezer and allow sample to return to room temperature
5. Put in −40° C. freezer over the weekend
6. Remove from freezer and allow sample to return to room temperature
7. Add 5 μL of sample to 1 mL of EtOH, with mixing
8. Add 10 μL of dilution to 0.75 mL LCMS grade water and 0.25 mL of LCMS grade acetonitrile LCMS Column Gradient

| Solvent A Water with 1% Formic Acid Solvent B Acetonitrile with 1% Formic Acid | | | |
|---|---|---|---|
| Time (min) | Flow (mL/min) | % A | % B |
| 0 | 0.7 | 80 | 20 |
| 9 | 0.7 | 2 | 98 |
| 10 | 0.7 | 2 | 98 |
| 12 | 0.7 | 80 | 20 |

Figure 11:
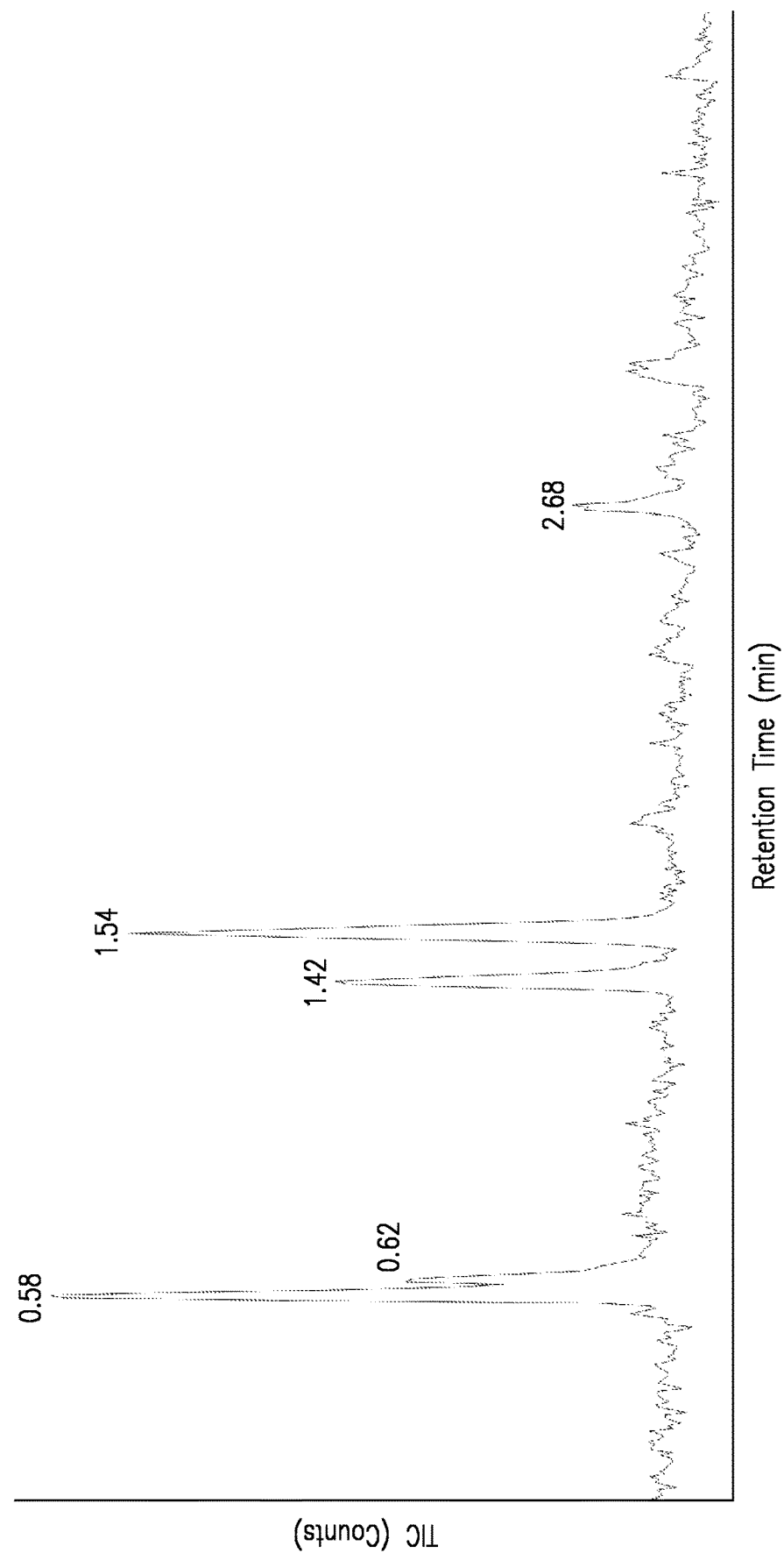
FIG. 11 is a spectrum derived from the assay described in Example 11.

FIG. 11 is the spectrum generated in this example. The following table lists the retention times, the areas under the important peaks, the % areas, and the mass of the corresponding reaction products.

| Retention Time (min) | Area | % Area | Mass |
|---|---|---|---|
| 0.58 | 23086000 | 29.61 | 214 |
| 0.62 | 9346882 | 11.99 | 212 |
| 1.42 | 15029988 | 19.28 | 378 |
| 1.54 | 25596606 | 32.83 | 378 |
| 2.68 | 4905235 | 6.29 | 524 |

With approximately 52.11% with the mass 378.

Conclusions

As is evident from the spectra and the area data from the tables of the examples, the low-temperature syntheses gave significantly higher quantities of the desirable end products having molecular weights of from about 360-380, and more particularly 360, 376, and 378. The initial peak in each case was residual harmaline (mass 214) and the products other than the desired products were very low in % Area and hence weight amounts. Thus, the low-temperature synthesis methods of the invention give much improved reaction product syntheses as compared with prior high-temperature methods.

Example 12

The reaction between harmaline and thymoquinone can take place either at the carbonyl carbon or the carbon next to the carbonyl group of thymoquinone and can give a mixture of four isomers, see FIG. 12.

We calculated the thermodynamic properties of reactants and products to obtain reaction energetics using the Density functional theory (DFT) method. DFT calculations were performed on four GZ-725 isomers for geometry optimization and the corresponding partial charges using the Gaussian package. We used the B3LYP functional and 6-311+G(d) basis set for the geometry optimization and charge calculations. The potential-derived atomic charges were calculated using CHELPG procedure. All optimized structures were checked by analyzing harmonic vibration frequencies. The optimized structures of all investigated molecules are at the stationary points corresponding to local minima without imaginary frequency.

Table 1 shows the calculated thermal enthalpy ($\Delta H$), entropy ($\Delta S$) and Gibbs free energy ($\Delta G$) for the reaction. DFT calculations indicate that the reaction of harmaline at the carbon next to the carbonyl group of thymoquinone, isomer 1 and 2 is thermodynamically more favorable and has smaller values of $\Delta H$ and $\Delta G$ than the reaction at the carbonyl carbon in isomer 3 and 4. Enol Isomer 1b is the most stable reaction product having the lowest value of Gibbs free energy ($\Delta G = -13.46$ kcal/mol) and also indicates the stability of reaction and a shift in equilibrium for enols.

Density functional theory (DFT) calculations indicated that (1) the reaction taking place at the carbon atom next to carbonyl group is thermodynamically more favorable, and (2) stability of reaction and a shift in equilibrium is for enols.

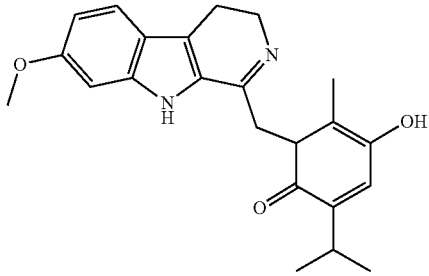

Chemical Formula: $C_{23}H_{26}N_2O_3$
Exact Mass: 378.19
Molecular Weight: 378.47

5-Hydroxy-7-(7-methoxy-4,9-dihydro-3H-β-carbolin-1-yl)-6-methyl-m-mentha-3,5-dien-2-one

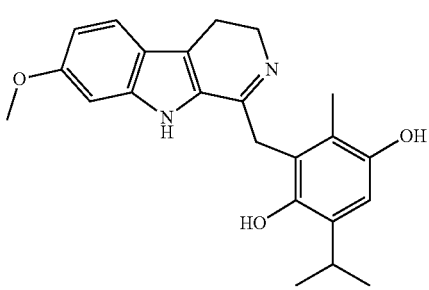

Chemical Formula: $C_{23}H_{26}N_2O_3$
Exact Mass: 378.19
Molecular Weight: 378.47

4-Isopropyl-6-[(7-methoxy-4,9-dihydro-3H-β-carbolin-1-yl)methyl]-1-methyl-2,5-benzenediol Hence, as illustrated in FIG. 12, isomer 1b (MW 378) is the most stable reaction product having the value of Gibbs free energy ($\Delta G = -13.46$ kcal/mol).

Example 13

GZ 725 isomers have been extracted by treating the crude reaction solution with DI water and/or sodium bicarbonate. GZ 725 isomers have also been extracted by recrystallisation using solvents like ethanol or methanol.

TABLE

Calculated thermal enthalpy (H), entropy (S), and change in reaction enthalpy ($\Delta H$), entropy ($\Delta S$) and Gibbs free energy ($\Delta G$).

| GZ-725 | H (kcal/mol) | S (kcal/mol) | $\Delta H$ (kcal/mol) | $\Delta S$ (kcal/mol) | $\Delta G$ (kcal/mol) |
|---|---|---|---|---|---|
| 1a-378 | −769141.8394 | 0.096 | 5.809478322 | 0.025 | −1.64427168 |
| 1b-378 | −769154.2515 | 0.094 | −6.6026497 | 0.023 | −13.4600997 |
| 2a-378 | −769140.073 | 0.095 | 7.575916157 | 0.024 | 0.420316157 |
| 2b-378 | −769155.0748 | 0.091 | −7.42594151 | 0.020 | −13.3889415 |
| 3a-378 | −769134.4975 | 0.096 | 13.15133362 | 0.025 | 5.697583622 |
| 4a-378 | −769139.3563 | 0.093 | 8.292531435 | 0.022 | 1.733231435 |

We claim:

1. A composition comprising one or more of the following compounds, and the isomers, tautomers, solvates, esters, metal complexes, and salts thereof:

IA
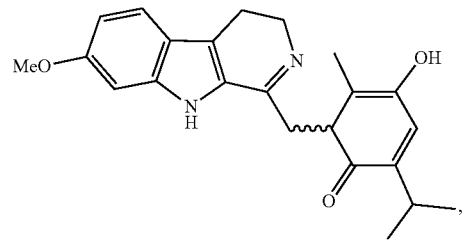

IIA
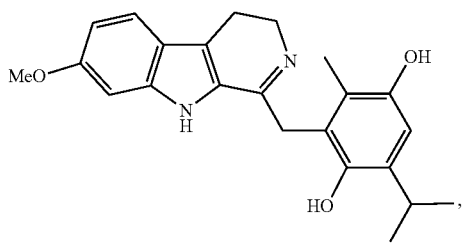

IIIA
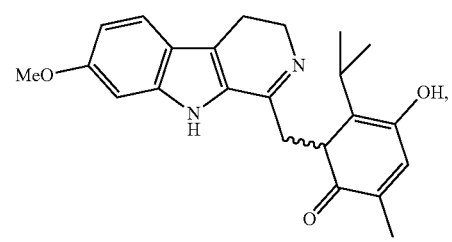

IVA
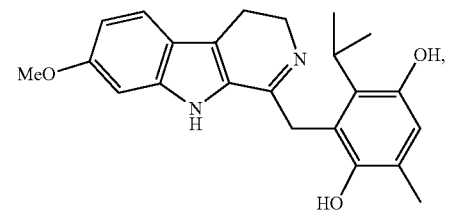

VAI
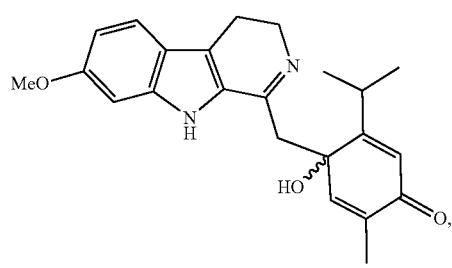

VAII
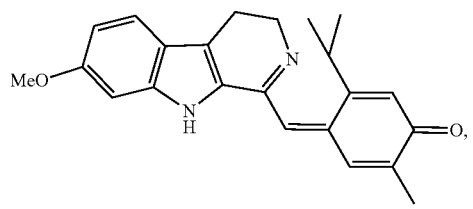

VIA
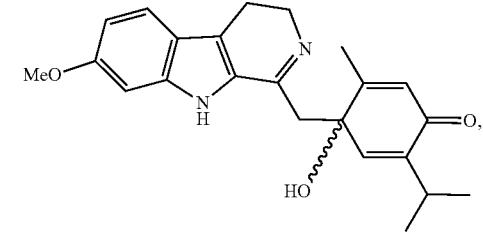

VIIA
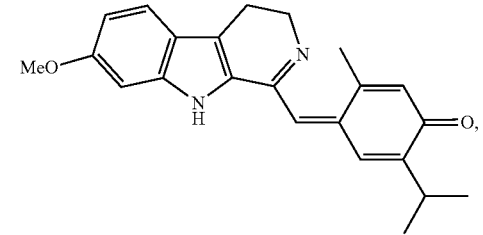

VIIIA
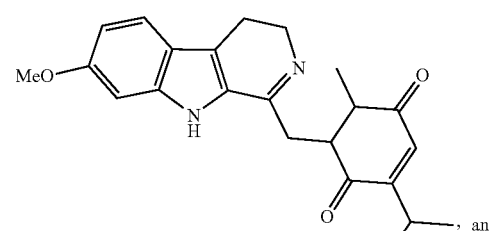

, and/or

IXA
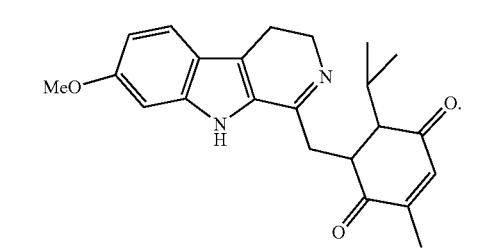

2. The composition of claim 1, said compound having a molecular weight of about 360 or about 378.

3. A method of treating a human suffering from cancer and/or diabetes, said method comprising administering a therapeutically-effective amount of a composition according to claim 1 to a human in need thereof.

4. The method of claim 3, said human being a diabetic patient.

5. The method of claim 3, said human being a cancer patient.

6. The method of claim 5, wherein said cancer patient is suffering from lymphoma.

7. A process for preparing a composition according to claim 1, said method comprising reacting harmaline and thymoquinone in a non-interfering solvent and carrying out the reaction between said thymoquinone and harmaline at a temperature of less than about 10° C. for at least 4 hours.

8. The process of claim 7, said reacting step comprises mixing together thymoquinone and harmaline in a noninterfering solvent to yield a reaction mixture and allowing said reaction mixture to stand at a temperature of less than about 10° C. for a time period of at least 4 hours.

9. The process of claim 8, wherein said reaction is carried out a temperature of less than about 0° C. for a time period from about 6 hours to about 100 hours.

10. The process of claim 8, wherein said thymoquinone and harmaline are mixed together in a weight ratio of from about 1:0.1 to about 1:2.

11. The process of claim 8, wherein said reaction is carried out a temperature of from about −18° C. to about −100° C. for a time period from about 6 hours to about 100 hours.

* * * * *